United States Patent
Grüner et al.

(10) Patent No.: US 10,391,043 B2
(45) Date of Patent: Aug. 27, 2019

(54) EFFECT PIGMENTS WITH HIGH CHROMA AND HIGH BRILLIANCY, METHOD FOR THE PRODUCTION AND USE THEREOF

(71) Applicant: Eckart GmbH, Hartenstein (DE)

(72) Inventors: Michael Grüner, Auerbach (DE); Günter Kaupp, Neuhaus (DE); Ralph Schneider, Lauf (DE)

(73) Assignee: ECKART GMBH, Hartenstein (DE)

( * ) Notice: Subject to any disclaimer, the term of this patent is extended or adjusted under 35 U.S.C. 154(b) by 0 days.

(21) Appl. No.: 15/536,220

(22) PCT Filed: Dec. 21, 2015

(86) PCT No.: PCT/EP2015/080862
§ 371 (c)(1),
(2) Date: Jun. 15, 2017

(87) PCT Pub. No.: WO2016/097417
PCT Pub. Date: Jun. 23, 2016

(65) Prior Publication Data
US 2017/0348201 A1 Dec. 7, 2017

(30) Foreign Application Priority Data

Dec. 19, 2014 (EP) ..................... 14199126

(51) Int. Cl.
*A61K 8/02* (2006.01)
*A61K 8/04* (2006.01)
(Continued)

(52) U.S. Cl.
CPC ............ *A61K 8/0266* (2013.01); *A61K 8/022* (2013.01); *A61K 8/042* (2013.01); *A61K 8/06* (2013.01);
(Continued)

(58) Field of Classification Search
CPC ... C09C 1/0015; C09C 1/0024; C09C 1/0051; C09C 1/0078; C09C 2200/102;
(Continued)

(56) References Cited

U.S. PATENT DOCUMENTS

| | | |
|---|---|---|
| 3,711,308 A | 1/1973 | Brand et al. |
| 5,017,207 A | 5/1991 | Watkinson et al. |

(Continued)

FOREIGN PATENT DOCUMENTS

| | | |
|---|---|---|
| CA | 2180669 A1 | 1/1997 |
| CN | 1312840 A | 9/2001 |

(Continued)

OTHER PUBLICATIONS

Byk-Gardner; Katalog; "Qualitatskontrolle tor Lacke und Kunststoffe" 2011/2012, pp. 97-98. In English and German.
(Continued)

*Primary Examiner* — Alexandre F Ferre
(74) *Attorney, Agent, or Firm* — The Webb Law Firm

(57) ABSTRACT

The invention relates to an absorbent effect pigment including a nonmetallic substrate in platelet form and a coating applied thereto, wherein the coating includes at least one spacer layer. The invention further relates to a process for production of and to the use of the absorbent effect pigment.

33 Claims, 5 Drawing Sheets

(51) Int. Cl.
  *A61K 8/06* (2006.01)
  *A61K 8/20* (2006.01)
  *A61K 8/26* (2006.01)
  *A61Q 19/00* (2006.01)
  *A61Q 1/04* (2006.01)
  *A61Q 1/06* (2006.01)
  *A61Q 1/10* (2006.01)
  *A61Q 3/02* (2006.01)
  *C09C 1/00* (2006.01)
  *A61Q 19/10* (2006.01)
  *A61Q 5/00* (2006.01)
  *A61K 8/29* (2006.01)

(52) U.S. Cl.
  CPC .......... *A61K 8/20* (2013.01); *A61K 8/26* (2013.01); *A61K 8/29* (2013.01); *A61Q 1/04* (2013.01); *A61Q 1/06* (2013.01); *A61Q 1/10* (2013.01); *A61Q 3/02* (2013.01); *A61Q 5/00* (2013.01); *A61Q 19/00* (2013.01); *A61Q 19/10* (2013.01); *C09C 1/009* (2013.01); *C09C 1/0015* (2013.01); *C09C 1/0024* (2013.01); *C09C 1/0051* (2013.01); *C09C 1/0078* (2013.01); *A61K 2800/10* (2013.01); *A61K 2800/413* (2013.01); *A61K 2800/436* (2013.01); *C01P 2002/52* (2013.01); *C01P 2002/85* (2013.01); *C01P 2004/03* (2013.01); *C01P 2004/51* (2013.01); *C01P 2004/52* (2013.01); *C01P 2004/61* (2013.01); *C01P 2006/63* (2013.01); *C01P 2006/64* (2013.01); *C01P 2006/65* (2013.01); *C09C 2200/102* (2013.01); *C09C 2200/1004* (2013.01); *C09C 2200/1033* (2013.01); *C09C 2200/1087* (2013.01); *C09C 2200/301* (2013.01); *C09C 2200/302* (2013.01); *C09C 2200/304* (2013.01); *C09C 2200/305* (2013.01); *C09C 2200/401* (2013.01); *C09C 2200/407* (2013.01); *C09C 2220/106* (2013.01)

(58) Field of Classification Search
  CPC ...... C09C 2200/1033; C09C 2200/305; C09C 220/401; C09C 2220/106
  See application file for complete search history.

(56) References Cited

U.S. PATENT DOCUMENTS

| | | | |
|---|---|---|---|
| 5,302,199 A * | 4/1994 | Prengel | B82Y 30/00 106/415 |
| 5,607,504 A | 3/1997 | Schmid et al. | |
| 5,624,486 A | 4/1997 | Schmid et al. | |
| 5,958,125 A | 9/1999 | Schmid et al. | |
| 6,113,873 A | 9/2000 | Tunashima et al. | |
| 6,261,469 B1 | 7/2001 | Zakhidov et al. | |
| 6,280,520 B1 | 8/2001 | Andes et al. | |
| 6,517,763 B1 | 2/2003 | Zakhidov et al. | |
| 6,569,529 B1 | 5/2003 | Phillips et al. | |
| 6,579,355 B1 | 6/2003 | Schmidt et al. | |
| 6,596,070 B1 | 7/2003 | Schmidt et al. | |
| 6,599,355 B1 | 7/2003 | Schmidt et al. | |
| 6,656,259 B2 | 12/2003 | Pfaff et al. | |
| 6,692,561 B1 | 2/2004 | Schoen et al. | |
| 6,719,838 B2 | 4/2004 | Heider et al. | |
| 6,840,993 B2 | 1/2005 | Schmidt et al. | |
| 7,169,222 B2 | 1/2007 | Bruckner et al. | |
| 7,241,503 B2 | 7/2007 | Noguchi | |
| 7,413,599 B2 | 8/2008 | Henglein et al. | |
| 7,604,862 B2 * | 10/2009 | Ambrosius | C09C 1/0024 252/301.6 R |
| 7,993,443 B2 | 8/2011 | Fuller et al. | |
| 7,993,444 B2 | 8/2011 | Fuller et al. | |
| 8,007,583 B2 | 8/2011 | Fuller et al. | |
| 8,383,531 B2 | 2/2013 | Fujiwara et al. | |
| 8,383,532 B2 | 2/2013 | Fujiwara et al. | |
| 8,500,901 B2 | 8/2013 | Rueger et al. | |
| 8,585,818 B1 | 11/2013 | Jones | |
| 8,715,407 B2 | 5/2014 | Schumacher et al. | |
| 8,728,226 B2 | 5/2014 | Schumacher et al. | |
| 8,728,227 B2 | 5/2014 | Schumacher et al. | |
| 8,728,228 B2 | 5/2014 | Schumacher et al. | |
| 9,051,471 B2 | 6/2015 | Gruner et al. | |
| 9,663,661 B2 | 5/2017 | Kaupp et al. | |
| 2002/0104461 A1 | 8/2002 | Schmidt et al. | |
| 2002/0169244 A1 | 11/2002 | Ostertag et al. | |
| 2003/0005859 A1 | 1/2003 | Andes et al. | |
| 2003/0039836 A1 | 2/2003 | Pfaff et al. | |
| 2003/0097965 A1 | 5/2003 | Heider et al. | |
| 2003/0205170 A1 | 11/2003 | Schmidt et al. | |
| 2003/0209169 A1 | 11/2003 | Andes et al. | |
| 2004/0003758 A1 | 1/2004 | Bruckner et al. | |
| 2004/0052743 A1 | 3/2004 | Schmidt et al. | |
| 2004/0139889 A1 | 7/2004 | Zimmermann et al. | |
| 2004/0144023 A1 | 7/2004 | Bruckner et al. | |
| 2004/0166316 A1 * | 8/2004 | Noguchi | C09C 1/0015 428/402 |
| 2004/0180010 A1 | 9/2004 | Andes et al. | |
| 2006/0027140 A1 | 2/2006 | Kniess et al. | |
| 2006/0042509 A1 | 3/2006 | Henglein et al. | |
| 2006/0225609 A1 | 10/2006 | Rueger et al. | |
| 2006/0254315 A1 | 11/2006 | Winkler et al. | |
| 2007/0104663 A1 | 5/2007 | Henglein et al. | |
| 2007/0199478 A1 | 8/2007 | Schlegl et al. | |
| 2007/0243149 A1 | 10/2007 | Hofacker et al. | |
| 2008/0181921 A1 | 7/2008 | DeLuca | |
| 2009/0264575 A1 | 10/2009 | Henglein et al. | |
| 2010/0047199 A1 | 2/2010 | Trummer et al. | |
| 2010/0095868 A1 | 4/2010 | Kaupp et al. | |
| 2010/0116169 A1 | 5/2010 | Kaupp et al. | |
| 2010/0175587 A1 | 7/2010 | Rueger et al. | |
| 2010/0297045 A1 | 11/2010 | Kaupp et al. | |
| 2011/0048276 A1 | 3/2011 | Schlegl et al. | |
| 2011/0160389 A1 | 6/2011 | Bubat et al. | |
| 2011/0226161 A1 | 9/2011 | Schumacher et al. | |
| 2011/0251293 A1 * | 10/2011 | Trummer | C03C 12/00 514/770 |
| 2011/0259243 A1 | 10/2011 | Schumacher et al. | |
| 2011/0265689 A1 | 11/2011 | Schumacher et al. | |
| 2011/0265690 A1 | 11/2011 | Schumacher et al. | |
| 2013/0149363 A1 | 6/2013 | Schmidt et al. | |
| 2013/0164356 A1 | 6/2013 | Pfaff et al. | |
| 2013/0216597 A1 | 8/2013 | Mathias et al. | |
| 2014/0018439 A1 | 1/2014 | Gruner et al. | |
| 2014/0251184 A1 | 9/2014 | McGuire et al. | |
| 2015/0259536 A1 | 9/2015 | Gruner et al. | |
| 2015/0344677 A1 | 12/2015 | Jones et al. | |
| 2016/0185972 A1 | 6/2016 | Schmidt | |

FOREIGN PATENT DOCUMENTS

| | | |
|---|---|---|
| CN | 1519278 A | 8/2004 |
| CN | 101289580 A | 10/2008 |
| CN | 102718229 A | 10/2012 |
| CN | 103183972 A | 7/2013 |
| CN | 104870571 A | 8/2015 |
| CN | 106536640 A | 3/2017 |
| DE | 1959998 A1 | 7/1971 |
| DE | 19836810 A1 | 2/2000 |
| DE | 102010021530 A1 | 12/2011 |
| DE | 102011012214 A1 | 8/2012 |
| EP | 0289240 B1 | 4/1992 |
| EP | 0668329 A2 | 8/1995 |
| EP | 0708154 A2 | 4/1996 |
| EP | 0723997 A1 | 7/1996 |
| EP | 0753545 A2 | 1/1997 |
| EP | 0870730 A1 | 10/1998 |
| EP | 0950693 A1 | 10/1999 |
| EP | 1029900 A1 | 8/2000 |
| EP | 1121334 A1 | 8/2001 |
| EP | 1213330 A1 | 6/2002 |
| EP | 1251152 A1 | 10/2002 |

(56) References Cited

FOREIGN PATENT DOCUMENTS

| | | | |
|---|---|---|---|
| EP | 1270682 A2 | 1/2003 |
| EP | 1281732 A1 | 2/2003 |
| EP | 1306412 A1 | 5/2003 |
| EP | 0948572 B1 | 7/2003 |
| EP | 1230310 B1 | 9/2003 |
| EP | 1375601 A1 | 1/2004 |
| EP | 1422268 A2 | 5/2004 |
| EP | 1230308 B1 | 8/2004 |
| EP | 1474486 A2 | 11/2004 |
| EP | 1546063 A1 | 6/2005 |
| EP | 1553144 A1 | 7/2005 |
| EP | 1572812 A1 | 9/2005 |
| EP | 1621585 A2 | 2/2006 |
| EP | 1685198 B1 | 5/2007 |
| EP | 1980594 B1 | 6/2009 |
| EP | 0948572 B2 | 1/2010 |
| EP | 1829833 B1 | 1/2010 |
| EP | 1699884 B1 | 2/2010 |
| EP | 1025168 B2 | 8/2010 |
| EP | 1587881 B1 | 12/2010 |
| EP | 2217664 B1 | 6/2011 |
| EP | 2371908 A2 | 10/2011 |
| EP | 2508571 A1 | 10/2012 |
| EP | 2042474 B1 | 3/2013 |
| EP | 2576702 A1 | 4/2013 |
| EP | 2346949 B1 | 7/2013 |
| EP | 2346950 B1 | 7/2013 |
| EP | 2356181 B1 | 7/2013 |
| EP | 2367889 B1 | 7/2013 |
| EP | 2698403 A1 | 2/2014 |
| EP | 2632988 B1 | 10/2014 |
| WO | 9638505 A1 | 12/1996 |
| WO | 0021905 A1 | 4/2000 |
| WO | 03006558 A2 | 1/2003 |
| WO | 1114103 B1 | 10/2003 |
| WO | 2004031102 A1 | 4/2004 |
| WO | 2004055119 A1 | 7/2004 |
| WO | 2004087816 A2 | 10/2004 |
| WO | 2006021386 A1 | 3/2006 |
| WO | 2006136435 A2 | 12/2006 |
| WO | 2007115675 A2 | 10/2007 |
| WO | 2008077612 A2 | 7/2008 |
| WO | 2009144005 A1 | 12/2009 |
| WO | 2011147892 A1 | 12/2011 |
| WO | 2012130897 A1 | 10/2012 |
| WO | 2014053454 A1 | 4/2014 |
| WO | 2014094993 A1 | 6/2014 |
| WO | 2015183674 A1 | 12/2015 |

OTHER PUBLICATIONS

U.S. Appl. No. 15/536,206, "Effect Pigments Having High Transparency, High Chroma and High Brilliancy, Method for the Production and Use Therof", filed Dec. 21, 2015.
U.S. Appl. No. 15/536,364, "Gold-Coloured Effect Pigments Having High Chroma and High Brilliancy, Method for the Production and Use Thereof", filed Dec. 21, 2015.
U.S. Appl. No. 15/536,945, "Metal Effect Pigments with High Chroma and High Brilliancy, Method for the Production and Use Thereof", filed Dec. 21, 2015.
U.S. Appl. No. 15/536,983, "Red-Coloured Decorative Pigments with High Chroma and High Brilliancy, Method for Their Production and Use of Same", filed Dec. 21, 2015.
U.S. Appl. No. 62/004,007, filed May 28, 2014.

\* cited by examiner

→ Height $h_a$ of the spacer layer

Substrate in platelet form

→ 6/6 no spacer layer permitted
→ 2/6 to 5/6 spacer layer permitted
→ 1/6 no spacer layer permitted

EFFECT PIGMENTS WITH HIGH CHROMA AND HIGH BRILLIANCY, METHOD FOR THE PRODUCTION AND USE THEREOF

CROSS-REFERENCE TO RELATED APPLICATIONS

The present application is the national phase of PCT/EP2015/080862 filed Dec. 21, 2015 and claims priority to European Patent Application No. 14199126.5 filed Dec. 19, 2014, the entire disclosures of which are hereby incorporated by reference herein.

BACKGROUND OF THE INVENTION

Field of the Invention

The present invention relates to absorbent effect pigments comprising a nonmetallic substrate in platelet form and a coating applied thereto, wherein the coating comprises at least one spacer layer, and to a process for production and to the use thereof.

Description of Related Art

Multilayer pigments which, based on a nonmetallic substrate in platelet form, comprise at least one layer sequence composed of layers of alternately high, low and high refractive index are known, for example, from EP 1 572 812 A1, EP 1 213 330 A1, EP 1 025 168 B2, EP 1 621 585 A2, EP 0 948 572 A1, EP 0 950 693 A1, EP 1 306 412 A1, EP 1 587 881 A2, EP 2 632 988 A1 or EP 1 474 486 A2. Depending on the optical layer thickness of the layer of low refractive index, it is possible for the multilayer pigments to change their visual appearance depending on the viewing angle, as described, for example, in EP 1 375 601 A1, EP 1 281 732 A1, EP 0 753 545 A2, US 2004/0003758 A1. A common factor in all the applications cited above is that the layer sequence includes a layer of low refractive index composed of a metal oxide of low refractive index, for example silicon oxide.

Compared to monolayer effect pigments with just a single identical first layer, multilayer pigments feature higher gloss and in some cases higher chroma, naturally assuming that the substrate and particle size here are the same.

EP 1 029 900 A1 discloses pigments which have been coated with (A) a pseudobrookite coating of high refractive index, consisting of a mixture of $TiO_2$ and $Fe_2O_3$ in a ratio of 10:1 to 1:3 and optionally one or more metal oxides in amounts of ≤20% by weight, based on the layer (A), (B) a colorless coating having a refractive index n≤1.8, and optionally an outer protective layer. The application does not contain any pointer to a spacer layer within or between layers (A) and (B).

EP 1 230 308 A1 discloses pigments including at least two layer sequences of (A) a colorless coating having a refractive index n≤1.8, (B) a coating of high refractive index composed of pseudobrookite consisting of a mixture of $TiO_2$ and $Fe_2O_3$ in a ratio of 1:0.1 to 1:5 and optionally one or more metal oxides in amounts of 20% by weight, based on the layer (B), and optionally (C) an outer protective layer. EP 1 230 308 A1 does not give any pointer to a spacer layer within or between layers (A) and (B).

EP 1 230 310 A1 discloses pigments comprising a layer sequence composed of (A) a coating of high refractive index, consisting of a mixture of $TiO_2$ and $Fe_2O_3$ in a ratio of 1:0.1 to 1:5 and optionally one or more metal oxides in amounts of ≤20% by weight, based on the layer (A), (B) a colorless coating having a refractive index n≤1.8, (C) a colorless coating having a refractive index n>1.8, (D) an absorbent coating having a refractive index n>1.8, and optionally (E) an outer protective layer. There is no description of a spacer layer within or between the aforementioned layers in EP 1 230 310 A1.

WO 2014/094993 A1 discloses interference pigments based on multiply coated substrates in platelet form which have, on the surface of the substrate, a layer sequence composed of (AO) optionally a layer composed of $TiO_2$, (A) a coating consisting of a mixture of $TiO_2$ and $Fe_2O_3$ which may optionally have been doped with one or more further oxides, (B) a layer composed of $SnO_2$, (C) a coating of high refractive index that absorbs in the visible wavelength range and optionally (D) an outer protective layer. In layer (A) and/or (C) the mixing ratio of $TiO_2$ to $Fe_2O_3$ is preferably 10:1 to 1:3. To increase the color intensity of the layer (A) and/or the layer (C), it is also possible to mix one or more oxides, for example $Al_2O_3$, $Ce_2O_3$, $B_2O_3$, $ZrO_2$, $SnO_2$, into the $TiO_2/Fe_2O_3$ mixture. WO 2014/094993 A1 does not disclose a spacer layer within or between the above-described layers.

CN 101289580 A describes the production of golden pigments having a strong interference color, the pigments being said to have the appearance of 24K gold. In this case, a mica substrate is suspended in water and a solution of $TiCl_4$ is added for coverage with a first layer, a solution of $FeCl_3$ and $TiCl_4$ for coverage with a second layer, a solution of $SnO_2$ for coverage with a third layer, and a solution of $TiCl_4$ for coverage with a fourth layer. After filtration and washing, the pigment is dried at 120° C. to 200° C. and calcined at 820° C. CN 101289580 A does not contain any pointer to a spacer layer in the coating.

EP 1 422 268 A2 discloses a pigment with multilayer structure, said pigment having two or more metal oxide layers, wherein the at least one metal (ion) of the metal oxide layer is selected from the group consisting of cerium, tin, titanium, iron, zinc and zirconium. The aim of this application is pigments having high chroma and high brilliance, and having a minimum number of pores of minimum size in their coating. According to EP 1 422 268 A2, a low pore volume is said to assure a coating of high visual quality.

US 2015/0344677 A1 relates to effect pigments based on coated substrates in platelet form. The coating comprises first and second layers of high refractive index, and a third component which is intended to diffuse partly or to an extent of 100% into one or both of the layers of high refractive index. The third component may be $SiO_2$ or another metal oxide. The aim of this application, in the case of effect pigments having a $D_{50}$ of 15 μm or less, is to obtain coverage with $SiO_2$ without agglomeration.

SUMMARY OF THE INVENTION

In some examples, there is provided an absorbent effect pigment comprising a nonmetallic substrate in platelet form and a coating applied to the substrate, wherein the coating comprises a) optionally a layer 1 comprising or consisting of at least one of tin oxide, tin hydroxide or tin oxide hydrate, b) a layer 2 comprising at least one of metal oxide, metal hydroxide or metal oxide hydrate, and c) a layer 3 comprising at least one of metal oxide, metal hydroxide or metal oxide hydrate, at least one of layers 2 and 3 comprises at least two different metal ions and layers 2 and 3 are interrupted by a spacer layer.

Also provided are processes for producing the absorbent effect pigment. Articles comprising at least one absorbent effect pigment of the present invention also are provided.

BRIEF DESCRIPTION OF THE DRAWINGS

The foregoing summary, as well as the following detailed description, will be better understood when read in conjunction with the appended drawings. In the drawings.

DETAILED DESCRIPTION

Figure 1:
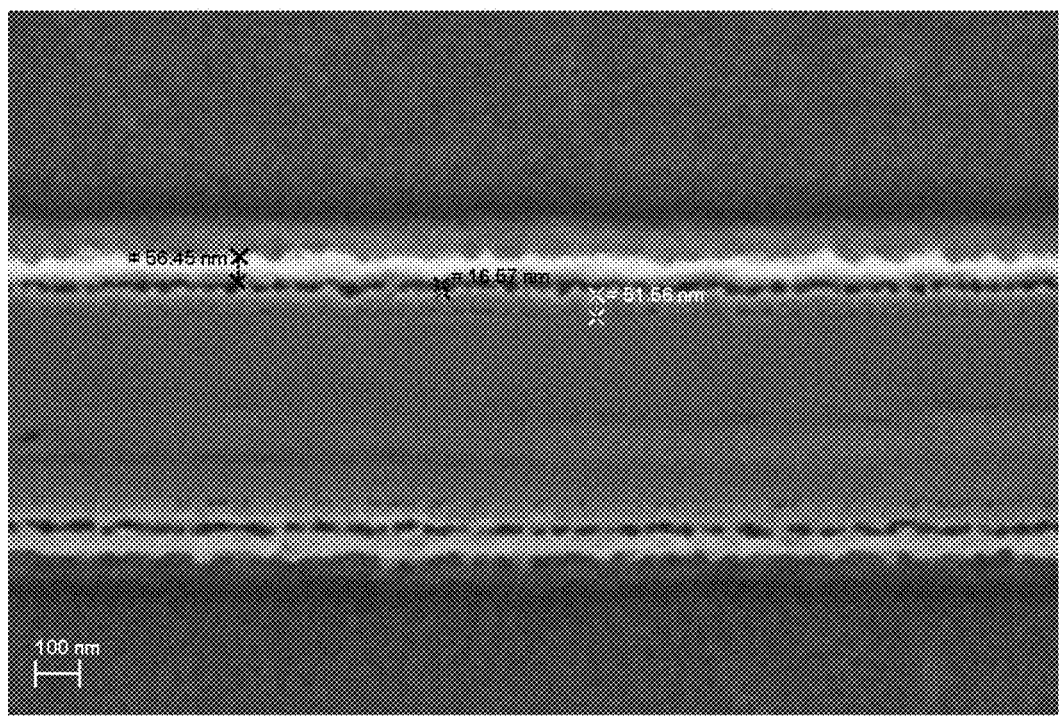
FIG. 1 is a scanning electron micrograph of a transverse section of an effect pigment of the invention in 50,000-fold magnification (based on Polaroid 545)

It was an object of the present invention to provide a high-chroma pigment having high gloss and high hiding power, which has high mechanical stability and high chemical stability and is simultaneously producible with low material input in a simple manner.

This object is achieved by providing an absorbent effect pigment comprising a nonmetallic substrate in platelet form and a coating applied to the substrate, wherein the coating includes a) optionally a layer 1 comprising or consisting of tin oxide, tin hydroxide and/or tin oxide hydrate, a) a layer 2 comprising at least one metal oxide, metal hydroxide and/or metal oxide hydrate, b) a layer 3 comprising at least one metal oxide, metal hydroxide and/or metal oxide hydrate, at least one of layers 2 and 3 comprises at least two different metal ions and layers 2 and 3 are interrupted by a spacer layer.

What is meant by "interrupted" in accordance with the invention is that layers 2 and 3 are spaced apart or kept at a distance from one another by a spacer layer.

What is meant by the general expression "metal oxide, metal hydroxide and/or metal oxide hydrate" in accordance with the invention is "metal oxide and/or metal hydroxide and/or metal oxide hydrate". This is also true when the metal or metal ion is specified, for example as titanium (ion), iron (ion), tin (ion), zirconium (ion) etc.

What is meant by the expression "a metal ion" or "an iron ion" in accordance with the invention is not one single metal ion or iron ion, but a multitude of metal ions or iron ions.

In a preferred embodiment, the optional layer 1 directly adjoins the nonmetallic substrate in platelet form, layer 2 directly follows layer 1 and layer 3 follows layer 2, with layers 2 and 3 interrupted by a spacer layer.

In a further embodiment, layer 2 directly adjoins the nonmetallic substrate in platelet form and layer 3 follows layer 2, with layers 2 and 3 interrupted by a spacer layer.

Preferred developments of the absorbent effect pigment are specified in dependent claims 2 to 9.

The object is additionally achieved by provision of a process for producing the absorbent effect pigment of the invention, wherein the process comprises the following steps:

(i) optionally applying an uncalcined layer comprising or consisting of tin oxide, tin hydroxide and/or tin oxide hydrate to the nonmetallic substrate in platelet form, (ii) sequentially applying three uncalcined layers A, B and C each consisting of or comprising at least one metal oxide, metal hydroxide and/or metal oxide hydrate, where the layers A, B and C are arranged directly one on top of another and where the at least one metal oxide, metal hydroxide and/or metal oxide hydrate applied in the layer B, in relation to the metal ion, is different than the metal ion(s) of the metal oxides, metal hydroxides and/or metal oxide hydrates of layer A and layer C, (iii) calcining the product obtained in step (ii) at a temperature from a range from 600° C. to 1000° C. to obtain the absorbent effect pigment comprising at least one spacer layer.

The object is alternatively achieved by provision of a process for producing the absorbent effect pigment of the invention, wherein the process comprises the following steps:

(i) sequentially applying two uncalcined layers B and C each consisting of or comprising at least one metal oxide, metal hydroxide and/or metal oxide hydrate to a calcined, singly or multiply coated nonmetallic substrate, where the layers B and C are arranged directly one on top of another and where the at least one metal oxide, metal hydroxide and/or metal oxide hydrate applied in the layer B, in relation to the metal ion, is different than the metal ion(s) of the metal oxide, metal hydroxide and/or metal oxide hydrate of layer C and of the layer which directly adjoins layer B in the substrate direction, (ii) calcining the product obtained in step (i) at a temperature from a range from 600° C. to 1000° C. to obtain the absorbent effect pigment comprising at least one spacer layer.

The invention further provides for the use of the absorbent effect pigment of the invention in cosmetic formulations, plastics, films, textiles, ceramic materials, glasses, paints, printing inks, writing inks, varnishes, powder coatings and/or in functional applications, for example for laser marking, IR reflection, photocatalysis.

The object underlying the invention is additionally achieved by provision of an article, wherein the article includes at least one absorbent effect pigment of the invention.

The nonmetallic substrates in platelet form that are to be coated may be selected from the group consisting of natural mica platelets, synthetic mica platelets, iron mica platelets, glass platelets, iron oxide platelets, $SiO_2$ platelets, $Al_2O_3$ platelets, kaolin platelets, talc platelets and bismuth oxychloride platelets. According to the invention, the absorbent effect pigments may also be based on mixtures of the above-specified nonmetallic substrates in platelet form. The aforementioned nonmetallic substrates in platelet form may also include one or more layers composed of or comprising at least one metal oxide, metal hydroxide and/or metal oxide hydrate of high and/or low refractive index. For instance, the substrates used may thus also be singly or multiply coated pearlescent pigments or interference pigments. In a preferred embodiment, the substrates to be used in accordance with the invention are uncoated nonmetallic substrates in platelet form.

The nonmetallic substrates in platelet form are preferably selected from the group consisting of natural mica platelets, synthetic mica platelets, glass platelets, $SiO_2$ platelets, $Al_2O_3$ platelets and mixtures thereof. The nonmetallic substrates in platelet form are more preferably selected from the group consisting of natural mica platelets, synthetic mica platelets, glass platelets and mixtures thereof. Very particularly preferred nonmetallic substrates in platelet form are synthetic mica platelets and/or glass platelets and mixtures thereof. Especially glass platelets are preferred as nonmetallic substrate in platelet form.

The glass platelets usable as substrate may, with regard to their composition, consist of silicate glass, such as soda-lime glass, lead crystal glass, E glass, A glass, C glass, ECR glass, Duran glass, window glass, laboratory glass, aluminosilicate glass or borosilicate glass. Preferably, the glass platelets have a composition corresponding to the teaching, especially corresponding to the main claim, of EP 1 980 594 B1, more preferably corresponding to the teaching, especially according to the respective main claims, of EP 1 829 833 B1 or EP 2 042 474 B1. The glass platelets usable as substrate are preferably produced by the process described in EP 289 240 B1.

In a further embodiment, the glass platelets can be colored in a controlled manner in the course of their production by the addition of at least one inorganic colorant. Suitable colorants are those that do not break down at the particular melting temperature of the glass composition. The proportion of colorant here is preferably within a range from 0.1% by weight to 50% by weight in total, more preferably within a range from 1% by weight to 35% by weight in total and most preferably within a range from 5% by weight to 25% by weight in total, based in each case on the total weight of the glass composition. Suitable colorants are especially elemental noble metals, such as Au, Pd or Pt, the cations or complex anions of the elements Cu, Cr, Mn, Fe, Ti and/or Co, and mixtures of the colorants listed above.

In a further embodiment, the refractive index of the glass platelets usable as substrate is within a range from 1.45 to 1.80, preferably within a range from 1.50 to 1.70.

In a further embodiment, the substrates in platelet form, especially glass platelets, may be ensheathed by a layer comprising or consisting of silicon oxide, silicon hydroxide, silicon oxide hydrate. For example, the aforementioned coating, in the case of use of glass platelets, can protect the glass surface from chemical alteration, such as swelling, leaching of glass constituents or dissolution in aggressive acidic coverage solutions.

The synthetic mica platelets usable as substrate may have a composition according to the main claim of CN 102718229 A or according to the main claim of US 2014/0251184 A1. They may additionally be produced according to the details in EP 0 723 997 A1, page 3 to page 4.

The synthetic mica platelets usable as substrate are preferably fluorphlogopite of the formula $KMg_3AlSi_3O_{10}F_2$, $KMg_2½(Si_4O_{10})F_2$ or $NaMg_2½(Si_4O_{10})F_2$, especially fluorphlogopite of the formula $KMg_3AlSi_3O_{10}F_2$, which, according to x-ray fluorescence analysis (XRF), preferably has the constituents specified in table 1 as the respective metal oxide within the ranges listed therein.

TABLE 1

Preferred compositions of synthetic mica platelets according to XRF Composition of synthetic mica platelets, figures in % by weight, based in each case on the total weight of the synthetic mica platelets

| | |
|---|---|
| $SiO_2$ | 38 to 46 |
| $Al_2O_3$ | 10 to 14 |
| $K_2O$ | 9 to 13 |
| $Fe_2O_3$ | 0.01 to 0.25 |
| MgO | 26 to 34 |
| MnO | 0 to 0.05 |
| $Na_2O$ | 0 to 13 |

The mean thickness of the nonmetallic substrates in platelet form that are to be coated is preferably within a range from 50 nm to 5000 nm, more preferably within a range from 60 nm to 3000 nm and most preferably within a range from 70 nm to 2000 nm. The mean thickness is understood in accordance with the invention to mean the arithmetic mean, unless stated otherwise.

In one embodiment, the mean thickness for glass platelets as the nonmetallic substrate in platelet form that is to be coated is within a range from 750 nm to 1500 nm, preferably within a range from 850 nm to 1400 nm and more preferably within a range from 900 nm to 1300 nm.

Thinner substrates in platelet form lead to a lower overall thickness of the absorbent effect pigments of the invention. Thus, likewise preferred as nonmetallic substrate in platelet form are glass platelets wherein the mean thickness is within a range from 50 nm to 700 nm, further preferably within a range from 101 nm to 600 nm, more preferably within a range from 160 nm to 500 nm and most preferably within a range from 200 nm to 400 nm.

In a further embodiment, the mean thickness of the natural or synthetic mica platelets as the nonmetallic substrate in platelet form that is to be coated is preferably within a range from 80 nm to 1300 nm, further preferably within a range from 90 nm to 1000 nm, more preferably within a range from 99 nm to 800 nm and most preferably within a range from 200 nm to 600 nm.

If nonmetallic substrates in platelet form are coated below a mean thickness of 50 nm with metal oxides of high refractive index, for example, extremely fracture-sensitive pigments are obtained, which can break up even on incorporation into the respective application medium, which in turn results in significant lowering of the gloss.

Above a mean substrate thickness of 5000 nm, the pigments can become too thick overall. This is associated with a poorer specific hiding capacity, meaning that the area covered per unit weight of absorbent effect pigment of the invention is lower. Moreover, such thick pigments have a lower degree of plane-parallel orientation to the substrate in the application medium. Poorer orientation in turn results in reduced gloss. With regard to tactile properties too, excessively thick effect pigments can be disadvantageous in an application.

In one embodiment, the relative standard deviation in the thickness distribution of the nonmetallic substrates in platelet form is 15% to 100%, preferably 17% to 70%, more preferably 19% to 61% and most preferably 21% to 41%.

The relative standard deviation in [%] is the quotient of calculated standard deviation and mean thickness.

The mean thickness of the nonmetallic substrate in platelet form is determined, using a cured lacquer film in which the absorbent effect pigments of the invention are aligned essentially plane-parallel to the substrate, according to the details below in section IIk "Determination of the mean thickness of the nonmetallic substrates in platelet form, the mean layer thickness of layers 2 and 3, the mean layer thickness of the overall coating, the mean height $h_a$ of the spacer layer and the mean height $h_H$ of the cavities". For this purpose, a transverse section of the cured lacquer film is examined under a scanning electron microscope (SEM), wherein the thickness of the nonmetallic substrate in platelet form is determined for at least 100 effect pigments and statistically averaged. According to the invention, the term "mean" always means the arithmetic mean, unless stated otherwise.

The scanning electron micrographs were obtained using transverse sections of the absorbent effect pigments of the invention with the Supra 35 scanning electron microscope (from Zeiss).

The absorbent effect pigments of the invention optionally comprise a layer 1 comprising or consisting of tin oxide, tin hydroxide and/or tin oxide hydrate. Layer 1 may optionally be present at least partly as a mixed layer with a layer directly adjoining layer 1, for example layer 2.

Layers 2 and 3 of the absorbent effect pigments of the invention, after calcination, are preferably each a layer of high refractive index, wherein the refractive index is preferably n>1.8, more preferably n≥1.9 and most preferably n≥2.1. According to the invention, the selection of the at least two different metal ions in layers 2 and 3 is made such that the metal oxide(s), metal hydroxide(s) and/or metal oxide hydrate(s) that form therefrom in layers 2 and/or 3 preferably each has or have an averaged refractive index of n>1.8.

The at least one metal oxide, metal hydroxide and/or metal oxide hydrate of layers 2 and 3 comprises at least two different metal ions, preferably selected from the group of metals consisting of Ti, Fe, Sn, Mn, Zr, Ca, Sr, Ba, Ni, Sb, Ag, Zn, Cu, Ce, Cr and Co, further preferably selected from the group of metals consisting of Ti, Fe, Sn, Mn, Zr, Ag, Zn, Cu and Ce, further preferably selected from the group of metals consisting of Ti, Fe, Sn, Ag, Zr and Ce, more preferably selected from the group of metals consisting of Fe, Sn, Ag, Zr and Ce, and most preferably selected from the group of metals consisting of Zr, Fe and Sn. According to the invention, the selection of the at least two different metal ions is made such that the resulting effect pigments of the invention are absorbent. "Absorbent effect pigments" is understood in the context of this invention to mean that the hiding quotient thereof, $D_q$, defined as $$D_q = \frac{L^{*25}_{black}}{L^{*25}_{white}},$$

is ≥0.41, preferably ≥0.45, more preferably ≥0.50 and most preferably ≥0.55. The hiding quotient is determined here using lacquer applications, on black/white hiding charts (Byko-Chart 2853, from Byk-Gardner), of a nitrocellulose lacquer (Erco 2615e bronze mixing lacquer colorless; from Maeder Plastiklack AG) which has been admixed with 6% by weight of the particular effect pigment of the invention, according to the details which follow in section IIc "Comparison of hiding". $L^{*25}_{black}$ and $L^{*25}_{white}$ here are the brightness values measured at a measurement angle of 25° on black and white backgrounds of the black/white hiding charts, preferably with the BYK-mac multi-angle colorimeter from Byk-Gardner.

The proportion of noncoloring metal ions selected from the group of metals consisting of Ti, Sn, Zr, Ca, Sr, Ba and Zn preferably totals 40% by weight, the proportion of noncoloring metal ions being more preferably within a range from 0.1% by weight to 35% by weight in total and more preferably within a range from 1% by weight to 24% by weight in total, and the proportion of coloring metal ions selected from the group of metals consisting of Fe, Ti, Sn, Mn, Ni, Sb, Ag, Cu, Ce, Cr and Co preferably totals 4% by weight, the proportion of coloring metal ions being more preferably within a range from 5% by weight to 80% by weight in total and most preferably within a range from 20% by weight to 72% by weight in total, determined by means of XRF in each case, calculated in each case as the elemental metal and based in each case on the total weight of the absorbent effect pigment of the invention. The weight ratio of noncoloring metal ions to coloring metal ions in the absorbent effect pigment of the invention here is preferably <20, further preferably <10, more preferably <1 and most preferably <0.8.

Coloring metal ions from the group of the metals Ti and Sn relate especially to Ti in the +3 or +2 oxidation state and Sn in the +2 oxidation state.

The at least two different metal ions are preferably present either in homogeneous distribution in layers 2 and/or 3 or form a gradient therein. In exceptional cases, the at least two different metal ions may also be present in inhomogeneous distribution in layers 2 and/or 3.

What is meant by "at least two different metal ions" in accordance with the invention is that at least two metal ions of different elements are present, for example titanium and iron ions, or titanium and tin ions, or titanium and zirconium ions, or iron and tin ions, or iron and zirconium ions, etc. The various metal ions may be present in layer 2 and/or layer 3 of the absorbent effect pigment of the invention in a mixture of metal oxides and/or metal hydroxides and/or metal oxide hydrates and/or else in mixed oxides and/or mixed hydroxides and/or mixed oxide hydrates. Layer 2 and/or layer 3 may comprise or consist of this mixture of metal oxides and/or metal hydroxides and/or metal oxide hydrates and/or mixed oxides and/or mixed hydroxides and/or mixed oxide hydrates.

Preferably, in accordance with the invention, in the case of use of the metal ions Ti and Fe, the component comprising iron ions in the respective layer is present in layer 2 and/or in layer 3 in the calcined absorbent effect pigment of the invention in the form of iron titanate, preferably in the form of pseudobrookite and/or pseudorutile.

In one embodiment, one of the two layers 2 and 3 comprises only one kind of metal ion, preferably selected from the group of metals consisting of Fe, Ti, Sn and Zr, more preferably consisting of Fe, Ti and Sn. Correspondingly, the respective other layer of the two layers 3 and 2 includes at least two different metal ions, preferably selected from the group of metals consisting of Ti, Sn, Zr and Fe, further preferably consisting of Ti, Sn and Fe.

In a preferred embodiment, both layer 2 and layer 3 comprise at least one metal oxide, metal hydroxide and/or metal oxide hydrate composed of or comprising at least two metal ions selected from the group of metals consisting of Ti, Sn, Zr and Fe, further preferably consisting of Ti, Sn and Fe.

In a further embodiment, the layers 2 and 3 interrupted by the spacer layer are virtually identical in respect of the particular composition.

If the absorbent effect pigments of the invention comprise at least one coloring metal ion selected from the group of metals consisting of Fe, Ti, Sn, Mn, Cu, Cr, Co, Ag and Ce, the proportion thereof, determined in each case by means of XRF and calculated in each case as the elemental metal, preferably totals ≥4% by weight, and is further preferably within a range from 6% by weight to 85% by weight in total, more preferably within a range from 8% by weight to 79% by weight in total and most preferably within a range from 10% by weight to 76% by weight in total, based in each case on the total weight of the absorbent effect pigment.

In a preferred embodiment, at least one of layers 2 and 3 comprises at least two different metal ions selected from the group of metals consisting of Ti, Fe, Sn, Mn, Zr, Ca, Sr, Ba, Ni, Sb, Ag, Zn, Cu, Ce, Cr and Co, where at least one of these two metal ions is selected from the group of metals consisting of Ti, Sn, Zr and Zn and where the proportion of coloring metal ions selected from the group of metals consisting of Fe, Ti, Sn, Mn, Cu, Cr, Co, Ag and Ce, determined in each case by means of XRF and calculated in each case as the elemental metal, preferably totals >4% by weight, based on the total weight of the absorbent effect pigment of the invention.

In a particularly preferred embodiment, at least one of layers 2 and 3 comprises metal oxides, metal hydroxides and/or metal oxide hydrates, where the metal ions of the metal oxides, metal hydroxides and/or metal oxide hydrates comprise or are the metals Ti and Fe, where the weight ratio of Ti to Fe, determined in each case by means of XRF and calculated in each case as the elemental metal, is <15, preferably <10, more preferably <5 and most preferably <1, and where the proportion of Fe, determined by means of XRF and calculated as the elemental metal, is preferably >4% by weight, based on the total weight of the absorbent effect pigment of the invention.

In a further particularly preferred embodiment, at least one of layers 2 and 3 comprises metal oxides, metal hydroxides and/or metal oxide hydrates, where the metal ions of the metal oxides, metal hydroxides and/or metal oxide hydrates comprise or are the metals Fe and Sn, where the weight ratio of Fe to Sn, determined in each case by means of XRF and calculated in each case as the elemental metal, is preferably from a range from 1 to 80, further preferably from a range from 2 to 60, more preferably from a range from 3 to 50 and most preferably from a range from 4 to 40, and where the proportion of Sn, determined by means of XRF and calculated as the elemental metal, is preferably selected from a range from 1% by weight to 25% by weight, further preferably from a range from 2% by weight to 19% by weight and more preferably from a range from 4% by weight to 15% by weight, based in each case on the total weight of the absorbent effect pigment of the invention.

In a further particularly preferred embodiment, at least one of layers 2 and 3 comprises metal oxides, metal hydroxides and/or metal oxide hydrates, where the metal ions of the metal oxides, metal hydroxides and/or metal oxide hydrates comprise or are the metals Fe and Zr, where the weight ratio of Fe to Zr, determined in each case by means of XRF and calculated in each case as the elemental metal, is selected from a range from 1 to 75, preferably from a range from 2 to 65, more preferably from a range from 4 to 48 and most preferably from a range from 8 to 36, based in each case on the total weight of the absorbent effect pigment of the invention.

The metal oxide, metal hydroxide and/or metal oxide hydrate contents of the absorbent effect pigments of the invention are determined as the respective metal oxide by means of x-ray fluorescence analysis (XRF) and can be calculated as the respective elemental metal. For this purpose, the absorbent effect pigment is incorporated into a lithium tetraborate glass tablet, fixed in solid sample measuring cups and analyzed therefrom. The measuring instrument used was the Advantix ARL system from Thermo Scientific.

The mean layer thickness of layer 1 is preferably less than 10 nm, more preferably less than 5 nm and most preferably less than 3 nm, with layer 1 completely ensheathing or incompletely ensheathing the nonmetallic substrate in platelet form or an optionally present coating.

The mean layer thickness of each of layers 2 and 3 of the absorbent effect pigments of the invention is preferably within a range from 30 nm to 350 nm, further preferably within a range from 35 nm to 310 nm, further preferably within a range from 90 nm to 340 nm, more preferably within a range from 40 nm to 280 nm and most preferably within a range from 50 nm to 210 nm.

In a preferred embodiment, the mean layer thickness of layers 2 and 3 is virtually the same. What is understood by "virtually the same mean layer thickness" in accordance with the invention is that the quotient of the mean layer thickness of layer 2 and the mean layer thickness of layer 3 is preferably within a range from 0.5 to 1.8, further preferably within a range from 0.7 to 1.6, more preferably within a range from 0.8 to 1.4 and most preferably within a range from 0.9 to 1.2.

In a further embodiment, in the case of a different physical composition of layers 2 and 3, the respective optical layer thickness thereof is virtually the same, where the optical layer thickness of layers 2 and 3 may or may not follow the known lambda/4 rule. The optical layer thickness is defined as the product of refractive index and mean layer thickness of the respective layer.

The mean layer thickness of the overall coating of the absorbent effect pigments of the invention is preferably ≤800 nm. The mean layer thickness of the overall coating is preferably within a range from 45 nm to 650 nm, more preferably within a range from 65 nm to 530 nm and most preferably within a range from 80 nm to 380 nm.

"Overall coating" is understood to mean the complete coating which proceeds from the substrate surface and extends perpendicularly therefrom in one direction.

In one embodiment, the relative standard deviation of the layer thickness distribution of layers 2 and 3 is 2% to 74%, preferably 3% to 63%, more preferably 4% to 57% and most preferably 5% to 49%, and the relative standard deviation of the layer thickness distribution of the overall coating is 0.3% to 31%, preferably 1% to 27%, more preferably 1.2% to 24% and most preferably 1.9% to 22%. The relative standard deviation in [%] is the quotient of calculated standard deviation and mean thickness.

The spacer layer between layers 2 and 3 is preferably arranged essentially parallel to the surface of the nonmetallic substrate in platelet form. What is understood by "essentially parallel" in the context of this invention is that, in a scanning electron micrograph of a transverse section, a regression line drawn through a spacer layer, in relation to a regression line drawn on the surface of the nonmetallic substrate in platelet form, has a slope of preferably close to 0.

Figure 7:
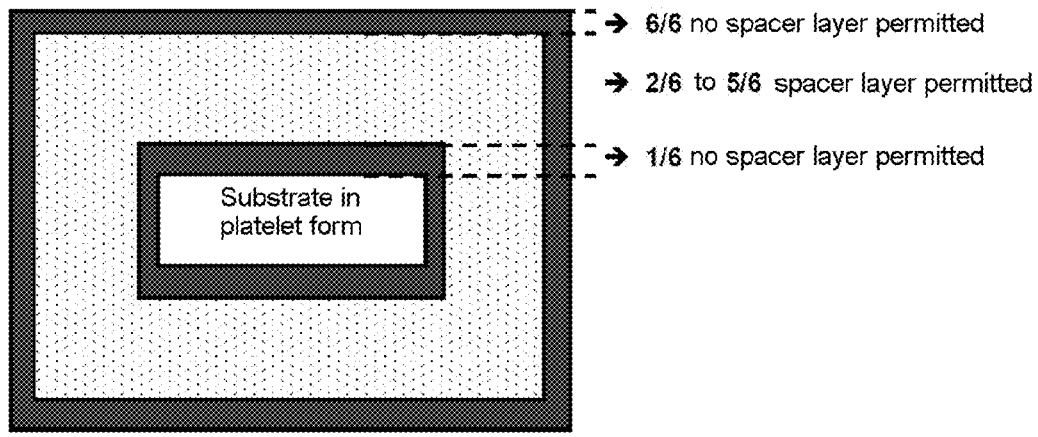
FIG. 7 is a schematic diagram of the position of the spacer layer.

The position of the spacer layer within the overall coating may vary. If, for example, the mean layer thicknesses of layers 2 and 3 are virtually identical, the spacer layer, in relation to the overall coating, preferably composed of optional layer 1 and layers 2 and 3, is in about the middle of the overall coating, since the optional layer 1 is preferably extremely thin, more preferably just a few atom layers thick. The spacer layer is preferably arranged between the first sixth and the sixth sixth of the overall coating in relation to the overall coating. The first sixth here refers to the proportion facing the nonmetallic substrate in platelet form, and the sixth sixth to the proportion of the overall coating remote from the nonmetallic substrate in platelet form (FIG. 7).

The spacer layer formed between layers 2 and 3 preferably has connections, which can also be referred to as spacers, which on the one hand connect the layers adjoining on either side of the spacer layer and on the other hand keep them spaced apart. As apparent from scanning electron micrographs of transverse sections, these connections or spacers, for example in the form of bars or columns, may be arranged at an angle of about 90°, for example of 80° to 100°, to the surface of the nonmetallic substrate in platelet form. However, they may also assume any other angle between 5° and 175°. Preferably, the spacers, especially bars, preferably the longitudinal axes of the spacers, preferably bars, are arranged at an angle from a range from 15° to 150° and more preferably at an angle from a range from 35° to 135°, in each case to the surface of the nonmetallic substrate in platelet form. In the determination of the angle, the substrate plane forms the first limb. One of the outsides of the bar in question in each case forms the second limb. The angle formed is determined proceeding from the angle vertex of the two limbs, with 0° being assumed to lie to the left and 180° to the right in the substrate plane in the top view of the scanning electron micrographs of transverse sections.

The connections or spacers may assume various geometric forms and are preferably distributed homogeneously over the entire spacer layer. For example, the connections or spacers may take the form of meshes, grids, ladders, sponges or honeycombs. It may also be possible to identify some structural elements similar to those in a photonic or inverse photonic crystal, as known, for example, from EP 2 371 908 A2, EP 1 546 063 A1 or EP 1 121 334 A1.

The connections or spacers comprise at least one metal oxide, metal hydroxide and/or metal oxide hydrate. In a preferred embodiment, the connections or spacers comprise an identical physical composition to the layers on either side of the spacer layer. It is also alternatively possible for a gradient between various metal oxides, metal hydroxides and/or metal oxide hydrates to be formed within the connections or spacers.

In a preferred embodiment, the connections or spacers comprise a metal oxide, metal hydroxide and/or metal oxide hydrate, where the metal ions of the metal oxides, metal hydroxides and/or metal oxide hydrates comprise or are at least two metal ions selected from the group of metals consisting of Ti, Fe, Sn, Mn, Zr, Ca, Sr, Ba, Ni, Ag, Zn, Cu, Ce, Cr and Co, further preferably from the group consisting of Ti, Fe, Sn, Mn, Zr, Ag, Zn, Cu and Ce, more preferably from the group consisting of Ti, Fe, Sn, Zr, Ag and Ce, and most preferably from the group consisting of Ti, Fe and Sn.

The inventors assume that the connections or spacers can also bring about mechanical stabilization of the adjoining layers and hence of the absorbent effect pigment of the invention. Probably because of the number of connections or spacers, the different angles and geometric forms that the compounds or spacers can assume within the spacer layer, and the distribution thereof in a preferably homogeneous manner over the full area of the spacer layer, a mechanically very stable effect pigment is formed. The adhesion between the overall coating and the nonmetallic substrate in platelet form is very good in the absorbent effect pigments of the invention. Even extreme shear conditions as occur in what is called the Waring blender test are withstood by the absorbent effect pigments of the invention without detectable damage. The procedure of the Waring blender test is described hereinafter in section IIf "Waring blender test".

As well as their surprisingly good mechanical stability, the absorbent effect pigments of the invention have excellent chemical stability, as elucidated in the details below in section IIg "Determination of chemical stability".

Figure 6:
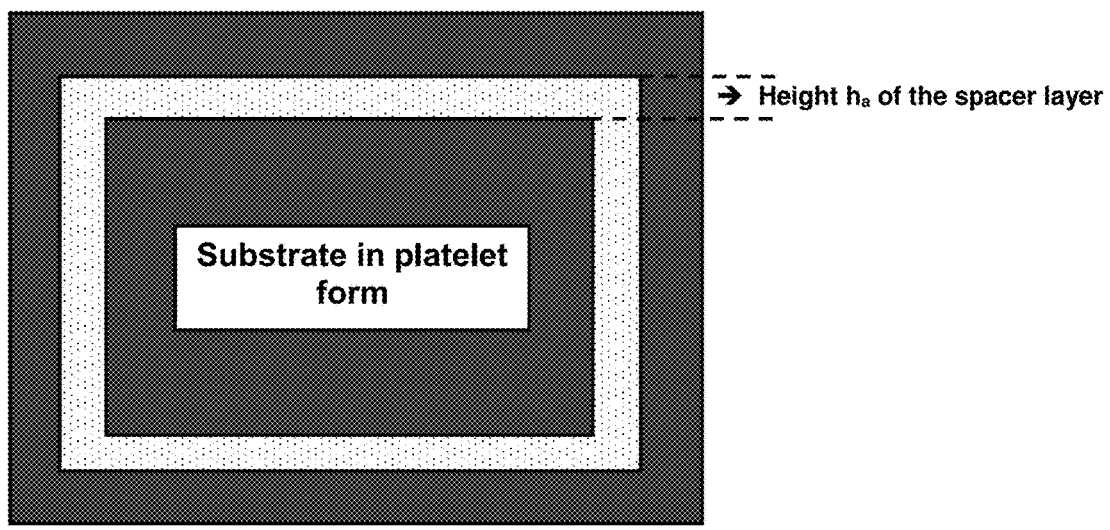
FIG. 6 is a schematic diagram of the spacer layer.

The spacer layer of the absorbent effect pigments of the invention preferably has a mean height $h_a$ from a range from 5 nm to 120 nm, further preferably from a range from 9 nm to 95 nm, further preferably from a range from 16 nm to 76 nm, further preferably from a range from 21 nm to 69 nm, more preferably from a range from 22 nm to 62 nm and most preferably from a range from 26 nm to 56 nm (FIG. 6).

To determine the mean height $h_a$ of the spacer layer, the mean layer thickness of layers 2 and 3 and the mean layer thickness of the overall coating, scanning electron micrographs of transverse sections are used to establish the upper and lower substrate surfaces as baselines. What is meant by the upper and lower substrate surfaces in the scanning electron micrographs of transverse sections is the longer side of the nonmetallic substrate in platelet form in each case. The baseline is drawn onto the scanning electron micrograph of the transverse section along the surface of the nonmetallic substrate in platelet form. The scanning electron micrographs of transverse sections were analyzed with the aid of the AxioVision 4.6.3 image processing software (from Zeiss).

Figure 4:
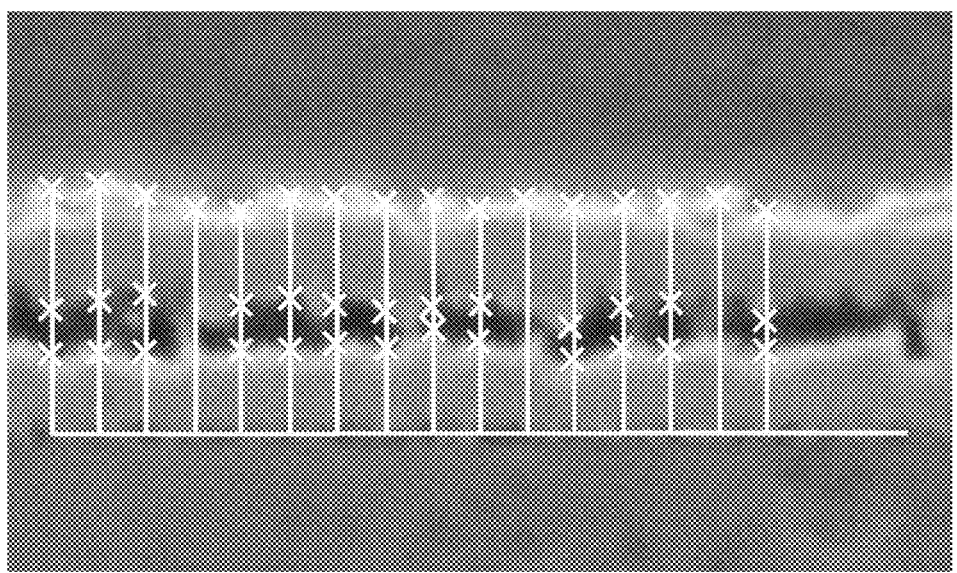
FIG. 4 is a detail of the scanning electron micrograph of a transverse section from FIG. 2 with a baseline drawn in at the interface of nonmetallic substrate in platelet form—coating, and lines arranged at right angles to the baseline. "x" marks the points of intersection at the interfaces.

A sufficient number of parallel lines are drawn at 50 nm intervals at a 90° angle from these two baselines as to place a grid over the effect pigment shown in the scanning electron micrograph of the transverse section (FIG. 4). The magnification of the scanning electron micrograph of the transverse section is preferably at least 50 000-fold, based on Polaroid 545 (4"×5"). Proceeding from the respective baseline of the nonmetallic substrate in platelet form, in the direction of the respective outer layer 3 or the respective outermost layer, the points of intersection between the parallel lines arranged at right angles to the respective baseline with the respective interfaces of the optional layer 1 with layer 2, of layer 2 with the spacer layer, of the spacer layer with layer 3, and of layer 3 with the environment or with any further layer applied are analyzed manually. It may be the case here that one of the lines drawn at 50 nm intervals occurs directly above a connection point or a spacer. In this case, only the respective point of intersection at the interface of layer 3 with the environment or with any further layer applied is recorded.

These measurements give rise to the layer thicknesses of layers 2 and 3, the layer thickness of the overall coating, the layer thickness of further layers optionally present, and the height $h_a$ of the spacer layer by formation of differences. The layer thickness of layer 2 is calculated from the difference between the respective measured points of intersection at the respective interfaces of layer 2 with the spacer layer and of either optional layer 1 with layer 2 or the baseline with layer 2 if the nonmetallic substrate in platelet form has not been covered with further layers beforehand. The layer thickness of layer 3 is calculated from the difference between the respective measured points of intersection of layer 3 with the environment or any further layer applied and of the spacer layer with layer 3. The layer thickness of the overall coating is calculated from the difference between the respective points of intersection of layer 3 with the environment or any further layer applied with the environment and the respective baseline. The height $h_a$ of the spacer layer is calculated from the difference between the respective measured points of intersection of spacer layer with layer 3 and layer 2 with the spacer layer. The layer thicknesses of any further layers applied can be determined analogously and should be taken into account correspondingly in forming the differences.

The individual values of the layer thicknesses and the height $h_a$ that have been determined in this way are used to form the respective arithmetic means in order to determine the above-specified values for the mean layer thicknesses and the mean height $h_a$. To be statistically meaningful, the above-described measurements are conducted on at least 100 of the parallel lines arranged at right angles to the baselines.

The height $h_{ma}$ refers to the midpoint of the spacer layer. It is calculated as the sum total of the layer thickness of the optional layer 1 and of layer 2 and half the height $h_a$ of the spacer layer. The relative height $h_{Rma}$ of the midpoint of the spacer layer is formed from the ratio of $h_{ma}$ and the layer thickness of the overall coating. The standard deviation of the relative height $\sigma h_{Rma}$ is preferably within a range from 0.2% to 18%, further preferably within a range from 0.3% to 15%, more preferably within a range from 0.4% to 11% and most preferably within a range from 0.5% to 8%. The standard deviation of the relative height $\sigma h_{Rma}$ is a measure of the extent to which the spacer layer is in a defined position parallel to the surface of the nonmetallic substrate in platelet form over the entire coating.

If the absorbent effect pigments of the invention have at least one further spacer layer, the height $h_{ma}$ thereof and the relative height of the midpoint of the at least one further spacer layer $h_{Rma}$ thereof are ascertained via the above-described method using scanning electron micrographs of transverse sections. The above-specified values for standard deviation of the relative height $\sigma h_{Rma}$ apply correspondingly to further spacer layers.

Figure 5:
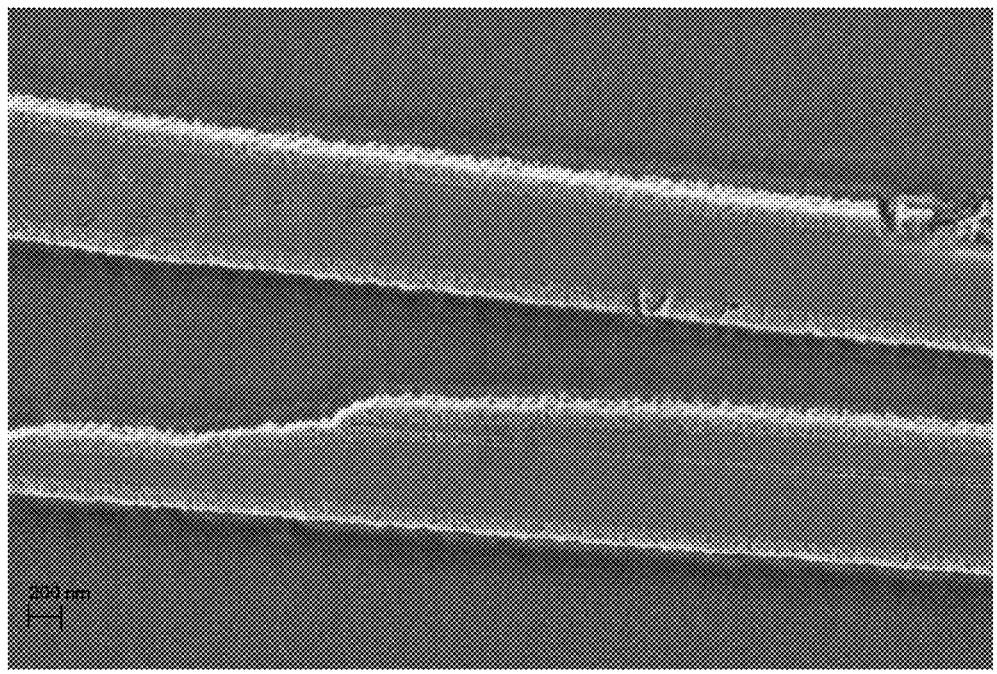
FIG. 5 is a scanning electron micrograph of a transverse section of the titanium dioxide-coated pearlescent pigment SYMIC C261 (from ECKART GmbH) in 20,000-fold magnification (based on Polaroid 545)

The person skilled in the art is aware that pearlescent pigments coated with titanium dioxide, for example, have pores in the coating that are statistically distributed over the entire coating (FIG. 5). These pearlescent pigments do not have a spacer layer. The spacer layer and the cavities present within the spacer layer in the absorbent effect pigments of the invention, by contrast, are not statistically distributed over the entire coating, but are arranged parallel to the surface of the nonmetallic substrate in platelet form over the entire coating.

The distances of the midpoints of the statistically distributed pores from the substrate surface were likewise determined by means of scanning electron micrographs of transverse sections by the method described above. For this purpose, a sufficient number of parallel lines were drawn at 50 nm intervals at a 90° angle with respect to the upper and lower baselines corresponding to the two surfaces of the substrate in platelet form that a grid has been placed over the pearlescent pigment without a spacer layer shown in the scanning electron micrograph of a transverse section. If one of the parallel lines occurred above one or more pores, the height(s) thereof, the pore midpoint(s) thereof and the distance of the pore midpoint(s) from the substrate surface were determined. The statistical distribution of the pore midpoints can likewise be used to determine a standard deviation.

The standard deviation of the distances of the midpoints of the statistically distributed pores from the substrate surface is >20% in pearlescent pigments from the prior art, i.e. in the case of pearlescent pigments without a spacer layer. The standard deviation of the distances of the midpoints of the statistically distributed pores from the substrate surface is thus distinctly different in terms of its value from the standard deviation of the relative height of the midpoint of the spacer layer of the absorbent effect pigments of the invention.

It is thus possible to compare the standard deviation of the distances of the pore midpoints from the substrate surface of pearlescent pigments without a spacer layer with the standard deviation of the relative height of the midpoint of the spacer layer of absorbent effect pigments of the invention.

In addition, with the aid of the above-described lines drawn at 50 nm intervals in a scanning electron micrograph, the number of connections or spacers per micrometer and the network density, defined as the number of connections or spacers per number of lines in %, is determined.

If the absorbent effect pigments of the invention have more than one spacer layer within the overall coating, the method just described for measuring the individual layers and the spacer layers is applied correspondingly.

In one embodiment, the relative standard deviation in the height distribution of the spacer layer is 4% to 75%, preferably 7% to 69%, more preferably 9% to 63% and most preferably 13% to 60%. The relative standard deviation in [%] of the height distribution is the quotient of the calculated standard deviation and the mean height.

In a preferred embodiment, the absorbent effect pigments of the invention, within the at least one spacer layer, have a number of connections or spacers per micrometer from a range from 0 to 11, further preferably from a range from 0 to 9, more preferably from a range from 1 to 7 and most preferably from a range from 1 to 3.

In a preferred embodiment, the absorbent effect pigments of the invention, within the at least one spacer layer, have a network density, defined as the number of connections or spacers per number of lines in percent, of <85%, preferably from a range from 1% to 75%, more preferably from a range from 1% to 63% and most preferably from a range from 1% to 49%.

Above a network density of 85%, in the context of this invention, reference is no longer made to a spacer layer since the high proportion of connections or spacers then leads to a very substantially continuous coating.

In a further preferred embodiment, the absorbent effect pigments of the invention comprise at least one spacer layer arranged essentially parallel to the surface of the nonmetallic substrate in platelet form, where the at least one spacer layer in each case has a mean height $h_a$ from a range from 19 nm to 83 nm, more preferably from a range from 27 nm to 66 nm and most preferably from a range from 33 nm to 57 nm.

In a particularly preferred embodiment, the absorbent effect pigments of the invention have at least one spacer layer of mean height $h_a$ from a range from 16 nm to 79 nm, preferably from a range from 21 nm to 66 nm and most preferably from a range from 23 nm to 57 nm, where the number of connections or spacers per micrometer within the at least one spacer layer is selected from a range from 0 to 8, preferably from a range from 0 to 6, more preferably from a range from 1 to 5 and most preferably from a range from 1 to 4.

The spacer layer comprises cavities as well as the above-described connections or spacers. These cavities are spatially bounded by layers 2 and 3 and the connections or spacers.

Energy-dispersive x-ray microanalysis (EDX analysis) of these cavities does not permit any conclusion as to whether the material is solid or liquid, and so the inventors are assuming, with the methods of analysis available at present, that the cavities within the spacer layer comprise a gas, probably air. The connections or spacers, by contrast, comprise at least one metal oxide, metal hydroxide and/or metal oxide hydrate, as detailed above.

The cavities within the spacer layer of the absorbent effect pigments of the invention may assume a mean height $h_H$ from a range from 2 nm to 119 nm, preferably from a range from 6 nm to 105 nm, more preferably from a range from 11 nm to 85 nm and most preferably from a range from 18 nm to 53 nm. The height $h_H$ is understood to mean the greatest difference between the uppermost and lowermost cavity boundaries. It is determined by the method described above for the height $h_a$, by drawing parallel lines at 50 nm intervals at a 90° angle to the surface of the nonmetallic substrate in platelet form in scanning electron micrographs of transverse sections. The difference of the two points of intersection of these lines with the upper and lower cavity boundaries is the height $h_H$. Here too, to be statistically meaningful, the above-described measurements are conducted on at least 100 lines. Therefore, the mean height $h_a$ is a maximum value for the mean height $h_H$. Accordingly, it is also possible for a plurality of cavities to be present one on top of another within the spacer layer.

The mean height of the spacer layer $h_a$ and the mean height of the cavities $h_H$ are determined, using a cured lacquer film in which the absorbent effect pigments of the invention are aligned essentially plane-parallel to the substrate, according to the details given in section IIk "Determination of the mean thickness of the nonmetallic substrates in platelet form, the mean layer thickness of layers 2 and 3, the mean layer thickness of the overall coating, the mean height $h_a$ of the spacer layer and the mean height $h_H$ of the cavities". For this purpose, a transverse section of the cured lacquer film is examined under a scanning electron microscope (SEM), as described above for $h_a$. As an alternative to these transverse sections, the absorbent effect pigments of the invention can be cut by means of the FIB method (FIB=focused ion beam). For this purpose, a fine beam of highly accelerated ions (for example gallium, xenon, neon or helium) is focused to a point by means of ion optics and guided line by line over the effect pigment surface to be processed. On impact with the effect pigment surface, the ions release most of their energy and destroy the coating at this point, which leads to removal of material line by line. It is also possible using the scanning electron micrographs that have then been recorded, by the method described above, to determine the mean height $h_a$, the mean layer thickness of layers 2 and 3 and the mean layer thickness of the overall coating. The mean thickness of the nonmetallic substrate in platelet form can also be determined using scanning electron micrographs of the effect pigments that have been cut by the FIB method.

In a further embodiment, the absorbent effect pigments of the invention comprise, within the spacer layer, distributed over the entire effect pigment and measured using scanning electron micrographs of transverse sections, an area proportion of cavities from a range from 51% to 99%, preferably from a range from 63% to 96%, more preferably from a range from 76% to 95% and most preferably from a range from 84% to 94%, and an area proportion of connections or spacers from a range from 1% to 49%, preferably from a range from 4% to 37%, more preferably from a range from 5% to 24% and most preferably from a range from 6% to 16%.

It is further preferable that the total volume occupied by the connections and spacers in the spacer layer is less than the total volume occupied by the cavities.

Preferably, the total volume occupied by the connections or spacers in the spacer layer is less than 50% by volume, further preferably less than 30% by volume, more preferably less than 20% by volume and most preferably less than 10% by volume of the total volume occupied by the cavities.

In the absorbent effect pigments of the invention, the cavities within the spacer layer, by contrast with the pores of the teaching according to EP 1 422 268 A2, are explicitly desired. According to EP 1 422 268 A2, a coating with low porosity and a minimum number of pores is required to obtain pigments having high chroma and high brilliance. The pigments according to EP 1 422 268 A2 do not have a spacer layer. According to the invention, the cavities that are not distributed randomly within the overall coating but are present essentially parallel to the surface of the nonmetallic substrate in platelet form within the spacer layer do not have any adverse effect on the optical properties of the absorbent effect pigments of the invention. On the contrary, the absorbent effect pigments of the invention, compared to pigments with a single-layer coating, feature higher gloss and higher chroma, naturally assuming the same nonmetallic substrate in platelet form, the same particle size and an identical first coating. At the same time, depending on the coating thickness and the type of coating, different interference colors and/or different absorption colors can be obtained.

The higher gloss and the higher chroma can be explained by the maximum difference in refractive index between the spacer layer and the adjoining layers, which, according to Fresnel's law, leads in each case to a maximum reflection of light at these interfaces. For the cavities, the basis used here is the refractive index of air of approximately 1. A light beam hitting the spacer layer is partly reflected at the interfaces thereof, the respective intensity of the reflection according to Fresnel's law being dependent on the difference in refractive index of the adjoining layers from the spacer layer. Since such partial reflection takes place at every single interface, the total reflection also increases with the number of interfaces. In absorbent effect pigments of the invention, a light beam is thus partly reflected on multiple occasions, the effect of which is much more intense gloss and much greater intensity of the interference color compared to conventional, singly coated pigments.

If the cavities are statistically distributed within the overall coating, i.e. not essentially parallel to the nonmetallic substrate in platelet form, there will be a variation in the optical path length within the overall coating. The result of this is that the interference conditions are not adequately fulfilled and hence there will be no amplification or extinction.

The gloss of the absorbent effect pigments of the invention is determined using white/black hiding cards with the aid of a Micro-Tri-Gloss gloss meter from Byk-Gardner, according to the details given hereinafter in section IId "Gloss measurements". The chroma of the absorbent effect pigments of the invention is likewise determined using white/black hiding cards with the BYK-mac multi-angle colorimeter (from Byk-Gardner), according to the details given hereinafter in section IIb "Angle-dependent color measurements". Further optical effects, such as sparkles and graininess, are determined according to the details given hereinafter in section IIe "Effect measurements".

In one embodiment, the absorbent effect pigments of the invention comprise, as well as the above-described layers 1, 2 and 3, further layers of high and/or low refractive index, which may be arranged, viewed from the nonmetallic substrate in platelet form, either below the optional layer 1 or layer 2 and/or above layer 3. These further layers may comprise metal oxides, metal hydroxides, metal oxide hydrates, where the metal ions of the metal oxides, metal hydroxides, metal oxide hydrates comprise or are at least one metal ion selected from the group of metals consisting of Ti, Fe, Sn, Mn, Zr, Ca, Sr, Ba, Ni, Ag, Zn, Cu, Ce, Cr and Co, preferably selected from the group of metals consisting of Ti, Fe, Sn, Zr, Ag, Zn, Cu, Ce, Cr and more preferably selected from the group of metals consisting of Ti, Fe and Sn. Moreover, these further layers may comprise semitransparent metals selected from the group consisting of Ag, Al, Cr, Ni, Au, Pt, Pd, Cu, Zn and Ti, preferably selected from the group consisting of Ag, Au and Cu, the alloys of each and/or mixtures thereof. According to the invention, the further layers are selected such that the proportion of coloring metal ions selected from the group of metals consisting of Fe, Ti, Sn, Mn, Cu, Cr, Co, Ag and Ce, determined in each case by means of XRF and calculated in each case as the elemental metal, preferably totals >4% by weight, and is further preferably within a range from 5% by weight to 82% by weight in total, more preferably within a range from 7% by weight to 72% by weight in total and most preferably within a range from 10% by weight to 68% by weight in total, based in each case on the total weight of the absorbent effect pigment. Moreover, the proportion of at least one semitransparent metal, determined by means of XRF, preferably totals ≥1% by weight, and is more preferably within a range from 2% by weight to 20% by weight in total and most preferably within a range from 3% to 12% by weight in total, based in each case on the total weight of the absorbent effect pigment. If the absorbent effect pigments of the invention comprise at least one coloring metal ion and at least one semitransparent metal, regardless of whether they are in the nonmetallic substrate in platelet form or in the coating, the proportion thereof preferably totals ≥5% by weight, based on the total weight of the absorbent effect pigment.

In one embodiment, each of the layers of the absorbent effect pigments of the invention may be provided with a dopant, where the dopant may comprise metal oxides, metal hydroxides and/or metal oxide hydrates, and the metal ions of the metal oxides, metal hydroxides and/or metal oxide hydrates comprise or are at least one metal ion selected from the group of metals consisting of Ca, Mg, Al, Ce, Zr or Sn, preferably Al, Zr or Sn. The proportion of dopant preferably totals ≤1% by weight, more preferably totals ≤0.5% by weight and most preferably totals ≤0.2% by weight, based in each case on the total weight of the absorbent effect pigments.

In a further embodiment, the overall coating of the absorbent effect pigments of the invention may, as well as the spacer layer, comprise at least one further spacer layer also arranged essentially parallel to the surface of the nonmetallic substrate in platelet form between layers 2 and 3. Preferably, the absorbent effect pigments of the invention have not more than four spacer layers within the overall coating, since the optical quality thereof then decreases. According to the invention, even when the absorbent effect pigment of the invention comprises more than one spacer layer, in relation to the overall coating, there is no spacer layer either in the first sixth or in the sixth sixth of the overall coating.

The absorbent effect pigments of the invention may have any median particle size $D_{50}$. The $D_{50}$ values of the absorbent effect pigments of the invention are preferably within a range from 3 µm to 350 µm. Preferably, the $D_{50}$ values of the absorbent effect pigments of the invention are within a range from 4 µm to 211 µm, further preferably within a range from 6 µm to 147 µm, more preferably within a range from 7 µm to 99 µm and most preferably within a range from 8 µm to 56 µm. Exceptionally preferably, the absorbent effect pigments of the invention have a $D_{50}$ from a range from 3 µm to 15 µm or from a range from 10 µm to 35 µm or from a range from 25 µm to 45 µm or from a range from 30 µm to 65 µm or from a range from 40 µm to 140 µm or from a range from 135 µm to 250 µm.

The $D_{10}$ values of the absorbent effect pigments of the invention preferably encompass a range from 1 µm to 120 µm. More preferably, the $D_{10}$ values of the absorbent effect pigments of the invention are within a range from 1 µm to 5 µm or within a range from 5 µm to 25 µm or within a range from 10 µm to 30 µm or within a range from 20 µm to 45 µm or within a range from 25 µm to 65 µm or within a range from 75 µm to 110 µm.

The $D_{90}$ values of the absorbent effect pigments of the invention preferably encompass a range from 6 µm to 500 µm. More preferably, the $D_{90}$ values of the absorbent effect pigments of the invention are within a range from 8 µm to 250 µm or within a range from 10 µm to 150 µm or within a range from 40 µm to 70 µm or within a range from 68 µm to 110 µm or within a range from 120 µm to 180 µm or within a range from 400 µm to 490 µm.

The $D_{10}$, $D_{50}$ and $D_{90}$ of the cumulative frequency distribution of the volume-averaged size distribution function, as obtained by laser diffraction methods, indicates that, respectively, 10%, 50% and 90% of the effect pigments analyzed have a volume-averaged diameter less than or equal to the value specified in each case. In this context, the size distribution curve of the absorbent effect pigments of the invention is determined using the Malvern Mastersizer 2000 instrument according to the manufacturer's instructions. The scattered light signals are evaluated by the Fraunhofer theory, which also includes diffraction and absorption characteristics of the particles.

In a preferred embodiment, the absorbent effect pigments of the invention have a span ΔD, defined as $\Delta D = D_{90} - D_{10}/D_{50}$, from a range from 0.7 to 2.0, preferably from a range from 0.7 to 1.5, further preferably from a range from 0.8 to 1.3, more preferably from a range from 0.8 to 1.2 and most preferably from a range from 0.85 to 1.1. The advantages of a narrow size classification in relation to color purity and/or gloss of the resulting effect pigments are described, for example, in EP 2 217 664 A1, EP 2 346 950 A1, EP 2 356 181 A1, EP 2 346 949 A1, EP 2 367 889 A1.

The absorbent effect pigments of the invention can be produced as follows:

suspending the nonmetallic substrates in platelet form in water at a temperature from a range from 50° C. to 100° C., optionally applying an uncalcined layer comprising or consisting of tin oxide, tin hydroxide and/or tin oxide hydrate by adding a water-soluble tin salt with simultaneous addition of a mineral alkali, sequentially applying three uncalcined layers A, B and C in the form of metal oxides, metal hydroxides and/or metal oxide hydrates by sequential addition of three water-soluble metal salts, in each case with simultaneous addition of mineral alkali, where the second water-soluble metal salt—for production of layer B—is different in relation to the metal ion than the two other water-soluble metal salts for production of layer A and layer C, separating the coated substrates from the coating solution(s), and optionally washing and/or optionally drying the coated substrates, calcining the coated substrates at temperatures from a range from 600° C. to 1100° C., preferably from a range from 625° C. to 930° C. and more preferably from a range from 750° C. to 890° C. to obtain the absorbent effect pigments of the invention comprising at least one spacer layer.

In a preferred embodiment, the absorbent effect pigments of the invention are produced by the above process.

The application, preferably deposition, of the respective metal oxides, metal hydroxides and/or metal oxide hydrates is preferably effected at a constant pH within a range from pH 1.4 to 10.0 depending on the metal salt.

In addition to the at least three sequentially applied, preferably deposited, metal oxides, metal hydroxides and/or metal oxide hydrates, it is of course also possible for further metal oxides, metal hydroxides and/or metal oxide hydrates to be applied beforehand and/or subsequently, such that further layers may be arranged beneath or above the layer sequence [optional layer 1/layer 2/spacer layer/layer 3].

In the course of calcining, there is surprisingly diffusion presumably of the metal ions present in the layer B into layer A and/or layer C to form mixed metal oxides and/or mixed metal hydroxides and/or metal oxide hydrates and/or mixtures of metal oxides and/or metal hydroxides and/or metal oxide hydrates in layer A and/or layer C. Because of the diffusion of the metal ions from layer B into layer A and/or layer C in the course of calcining, layers 2 and 3 of the invention and the intermediate spacer layer are formed, with at least one of the two layers 2 and 3 comprising at least two different metal ions. The originally three successively deposited layers A, B and C thus give rise, in the course of calcining, to layers 2 and 3 and the intermediate spacer layer, with at least one of the two layers 2 and 3 comprising at least two different metal ions.

It is assumed that the different mobility of the metal oxides, metal hydroxides and/or metal oxide hydrates with respect to one another in the course of calcining is one of the factors responsible for the formation of the spacer layer. In this context, the mobility of the metal ions present in layer B competes with the mobility of the metal ions present in layers A and/or C, assuming that the metal ions diffuse out of layer B into at least one of the adjoining layers A and/or C and the metal ions diffuse from at least one of layers A and/or C into layer B. The inventors are assuming at present that, if the mobility of the metal ions present in layer B during the calcination is higher than the mobility of the metal ions present in layers A and/or C, is one of the possible explanations for the formation of the spacer layer. Furthermore, it is assumed that a concentration gradient in relation to the metal ions promotes the formation of a spacer layer, i.e. when more mobile metal ions can diffuse out of layer B into one of the adjoining layers A and/or C than in the reverse direction. In summary, it has been found that the formation of a spacer layer is caused by a complex interplay of a wide variety of different further factors, for example entropic and/or enthalpic effects, during the calcination, but these have not yet been conclusively clarified. For the formation of at least one further spacer layer, the above considerations naturally apply correspondingly.

In a preferred embodiment, the first and third of the three sequentially applied, preferably deposited, metal oxides, metal hydroxides and/or metal oxide hydrates comprise at least one metal ion selected from the group of metals consisting of Fe, Ti and Sn. The first and third metal oxides, metal hydroxides and/or metal oxide hydrates, after application, respectively produce layer A and layer C. The second of the three sequentially applied, preferably deposited, metal oxides, metal hydroxides and/or metal oxide hydrates produces layer B and comprises at least one metal ion selected from the group of metals consisting of Fe, Sn, Zr and Ce, which is different than the metal ions of the metal oxides, metal hydroxides and/or metal oxide hydrates deposited for production of layer A and layer C. In layer A and layer C, the metal oxides, metal hydroxides and/or metal oxide hydrates applied, preferably deposited, may be the same or different in relation to the metal ion(s).

Alternatively, the absorbent effect pigments of the invention can be produced as follows:

suspending the calcined, singly or multiply coated nonmetallic substrates in platelet form in water at a temperature from a range from 50° C. to 100° C., sequentially applying two uncalcined layers B and C in the form of metal oxides, metal hydroxides and/or metal oxide hydrates by sequential addition of two water-soluble metal salts, in each case with simultaneous addition of mineral alkali, where the first water-soluble metal salt—for production of layer B—is different in relation to the metal ion than the other water-soluble metal salt for production of layer C and the layer that directly adjoins layer B in the substrate direction, separating the coated substrates from the coating solution(s), and optionally washing and/or optionally drying the coated substrates, calcining the coated substrates at temperatures from a range from 600° C. to 1100° C., preferably from a range from 625° C. to 930° C. and more preferably from a range from 750° C. to 890° C. to obtain the absorbent effect pigments of the invention comprising at least one spacer layer.

Here too, the application, preferably deposition, of the respective metal oxides, metal hydroxides and/or metal oxide hydrates is preferably effected at a constant pH within a range from pH 1.4 to 10.0 depending on the metal salt.

It is suspected that, in the course of calcining, the metal ions present in the layer B diffuse at least into layer C to form mixed metal oxides and/or mixed metal hydroxides and/or metal oxide hydrates and/or mixtures of metal oxides and/or metal hydroxides and/or metal oxide hydrates in layer C. Because of the diffusion of the metal ions from layer B into layer C, the calcining forms layer 3 of the invention and the spacer layer. The originally two successively deposited layers B and C thus give rise, in the course of calcining, to layer 3 and the spacer layer, with at least layer 3 comprising at least two different metal ions. Layer 2 is already present here. Layer 2 refers to the outermost layer of the calcined, singly or multiply coated nonmetallic substrate in platelet form which is used as starting material.

Figure 8:
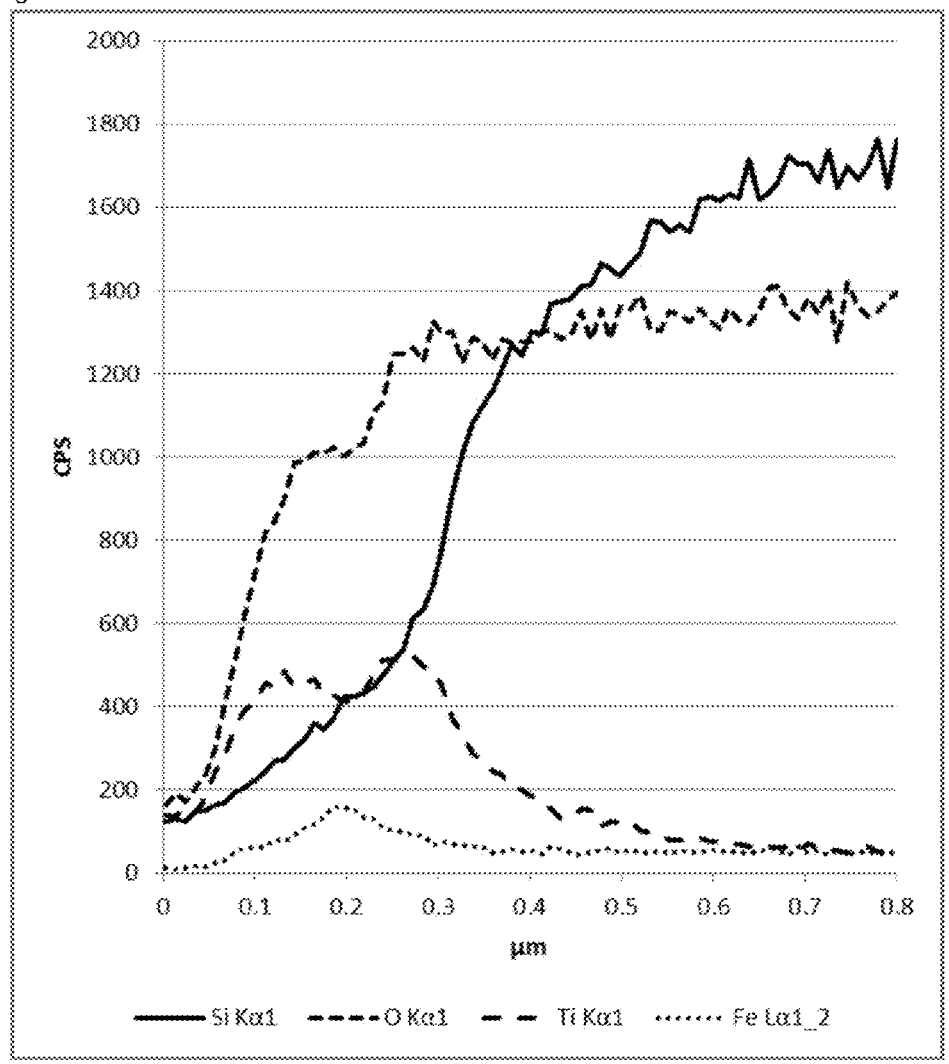
FIG. 8 is a concentration profile (line scan) using a transverse section in a scanning electron microscope with energy-dispersive microanalyzer (EDX) of example 12 prior to calcination.
Figure 9:
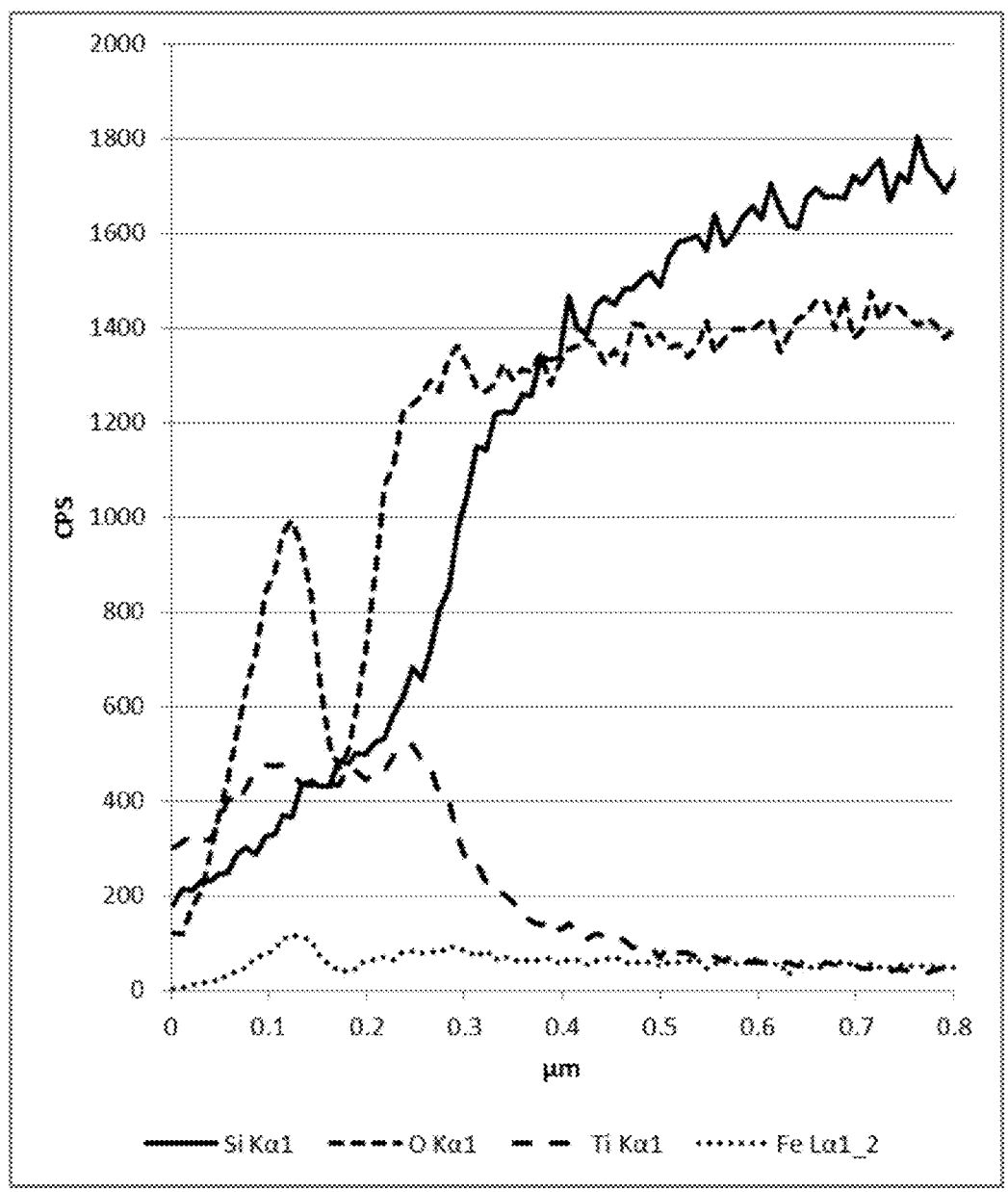
FIG. 9 is a concentration profile (line scan) using a transverse section in a scanning electron microscope with energy-dispersive microanalyzer (EDX) of example 12 after calcination.

The concentration profile (line scan) on the basis of transverse sections in the scanning electron microscope with an energy-dispersive microanalyzer (EDX) shows a significant location-dependent change in the chemical composition of the coating before and after calcination (FIGS. 8 and 9).

FIG. 8 shows a concentration profile of example 12 after coating and drying, but before calcination. Using the concentration curves of Ti and Fe, it is possible to recognize the maxima in each case of the Ti- and Fe-containing layers. The concentration curve of oxygen, by contrast, has a substantially homogeneous distribution without recognizable minima or maxima.

FIG. 9 likewise shows a concentration profile of example 12 after coating and drying, but after calcination. It is found that the Fe maximum present in FIG. 9 has been reduced and shifted. The Fe ions have diffused into the surrounding Ti-containing layers. What should additionally be emphasized is a marked minimum in the oxygen concentration curve which clearly indicates the position of the spacer layer. At the same position, there are corresponding minima in the concentration curves of Ti and Fe.

In a particularly preferred embodiment, the two or three sequentially applied, preferably deposited, metal oxides, metal hydroxides and/or metal oxide hydrates for production of the layers B and C or A, B and C do not comprise any metal ion(s) selected from the group of the metals consisting of Si, Mg and Al.

In the case of sequential application of two uncalcined layers B and C to an already coated and optionally calcined substrate, that layer to which the layer B is applied, in accordance with the invention, comprises a metal oxide, metal hydroxide and/or metal oxide hydrate of high refractive index.

In the case of sequential application of three uncalcined layers A, B and C to an already coated and optionally calcined substrate, that layer to which the layer A is applied, in accordance with the invention, may comprises a metal oxide, metal hydroxide and/or metal oxide hydrate of high or low refractive index.

The above remarks are elucidated in detail hereinafter by way of example with reference to various coatings.

If, for example, a water-soluble titanium(IV) salt, a water-soluble iron(III) salt and a water-soluble titanium(IV) salt again are applied successively to a suspension of an optionally coated nonmetallic substrate in platelet form, the calcination, viewed proceeding from the substrate in the SEM transverse section, following the coating which is optionally already present, gives rise to a layer 2 comprising a metal oxide, metal hydroxide and/or metal oxide hydrate, where the metal ions of the metal oxide, metal hydroxide and/or metal oxide hydrate comprise or are titanium ions and/or iron ions, a spacer layer, and a layer 3 comprising a metal oxide, metal hydroxide and/or metal oxide hydrate, where the metal ions of the metal oxide, metal hydroxide and/or metal oxide hydrate comprise or are titanium ions and/or iron ions. At least one of the layers comprising a metal oxide, metal hydroxide and/or metal oxide hydrate, where the metal ions of the metal oxide, metal hydroxide and/or metal oxide hydrate comprise or are titanium ions and/or iron ions, comprises an iron titanate, preferably pseudobrookite and/or pseudorutile. In relation to the amounts used, the above remarks relating to coloring and noncoloring metal ions are applicable here too.

If, for example, a water-soluble titanium(IV) salt is added to a suspension of the optionally coated nonmetallic substrate in platelet form and calcined following deposition of titanium dioxide, titanium hydroxide and/or titanium oxide hydrate, this product is resuspended after the calcination and a water-soluble iron(III) salt and a water-soluble tin(IV) salt are added successively, another calcination, viewed proceeding from the substrate in the SEM transverse section, following the coating which is optionally already present and layer 2 comprising a metal oxide, metal hydroxide and/or metal oxide hydrate, where the metal ion of the metal oxide, metal hydroxide and/or metal oxide hydrate comprises or is titanium ions, gives rise to a spacer layer and a layer 3 comprising a metal oxide, metal hydroxide and/or metal oxide hydrate, where the metal ion of the metal oxide, metal hydroxide and/or metal oxide hydrate comprises or is iron ions and/or tin ions.

If the absorbent effect pigments of the invention, in addition to the at least two or three sequentially applied, preferably deposited, metal oxides, metal hydroxides and/or metal oxide hydrates, include further layers comprising metal oxides, metal hydroxides and/or metal oxide hydrates, it is also possible for further spacer layers to form within the further layers, provided that the process steps described above for the at least two or three sequentially applied, preferably deposited, metal oxides, metal hydroxides and/or metal oxide hydrates are observed.

In one embodiment, the calcination is effected under reducing conditions, preferably in the presence of forming gas ($N_2/H_2$). A calcination under reducing conditions can be associated with lower brightness values L* than is the case for calcination under air.

The absorbent effect pigments of the invention may optionally be provided with at least one outer protective layer that further increases weathering stability and/or chemical stability and/or further reduces photoactivity. The UV stability and the condensate water stability were determined according to the details given below in the sections IIj "UV stability" and IIi "Condensate water test".

The optionally present protective layer comprises metal oxides, metal hydroxides and/or metal oxide hydrates wherein the metal ions are selected from the group of metals consisting of Si, Ce, Cr, Al, Zr, Zn and mixtures thereof, preferably from the group of metals Si, Ce, Al, Zr and mixtures thereof. In this context, the proportion of the optionally present protective layer is preferably within a range from 0.1% by weight to 7.0% by weight, more preferably within a range from 0.2% by weight to 5.2% by weight and most preferably within a range from 0.3% by weight to 3.1% by weight, based in each case on the total weight of the absorbent effect pigment of the invention.

The optionally present protective layer may additionally have been surface modified, for example by silanes. The silanes may have no functional bonding group or one or more functional bonding group(s). Silanes having at least one functional bonding group are also referred to hereinafter as organofunctional silanes.

For example, one or more silanes may have been applied to this outermost protective layer. The silanes may be alkylsilanes having branched or unbranched alkyl radicals having 1 to 24 carbon atoms, preferably 6 to 18 carbon atoms.

In a further preferred embodiment, the silane without a functional bonding group is an alkylsilane. The alkylsilane preferably has the formula $R_{(4-z)}Si(X)_z$. In this formula, z is an integer from 1 to 3, R is a substituted or unsubstituted, unbranched or branched alkyl chain having 10 to 22 carbon atoms, and X is a halogen and/or alkoxy group. Preference is given to alkylsilanes having alkyl chains having at least 12 carbon atoms. R may also be bonded to Si in a cyclic manner, in which case z is typically 2.

In a further embodiment, it is also possible to use at least one organofunctional silane which enables a chemical bond to a plastic, or a binder of a lacquer or a paint, etc., for surface modification. These groups of the organofunctional silane may also be referred to as coupling groups or functional bonding groups and are preferably selected from the group consisting of hydroxyl, amino, acryloyl, methacryloyl, vinyl, epoxy, isocyanate, cyano and mixtures thereof.

The organofunctional silanes having suitable functional groups that are used with preference as surface modifiers are commercially available and are produced, for example, by Evonik and sold under the "Dynasylan" trade name. Further products can be purchased from Momentive (Silquest silanes) or from Wacker, for example standard silanes and α-silanes from the GENIOSIL product group. Examples of these are 3-methacryloyloxypropyltrimethoxysilane (Dynasylan MEMO, Silquest A-174NT), vinyltri(m)ethoxysilane (Dynasylan VTMO and VTEO, Silquest A-151 and A-171), methyltri(m)ethoxysilane (Dynasylan MTMS and MTES), 3-mercaptopropyltrimethoxysilane (Dynasylan MTMO; Silquest A-189), 3-glycidoxypropyltrimethoxysilane (Dynasylan GLYMO, Silquest A-187), tris[3-(trimethoxysilyl)propyl]isocyanurate (Silquest Y-11597), bis[3-(triethoxysilyl)propyl)]tetrasulfide (Silquest A-1289), bis[3-(triethoxysilyl)propyl disulfide (Silquest A-1589), beta-(3,4-epoxycyclohexyl)ethyltrimethoxysilane (Silquest A-186), bis(triethoxysilyl)ethane (Silquest Y-9805), gamma-isocyanatopropyltrimethoxysilane (Silquest A-Link 35, GENIOSIL GF40), methacryloyloxymethyltri(m)ethoxysilane (GENIOSIL XL 33, XL 36), (methacryloyloxymethyl)(m)ethyldimethoxysilane (GENIOSIL XL 32, XL 34), (isocyanatomethyl)methyldimethoxysilane, (isocyanatomethyl)trimethoxysilane, 3-(triethoxysilyl)propylsuccinic anhydride (GENIOSIL GF 20), (methacryloyloxymethyl)methyldiethoxysilane, 2-acryloyloxyethylmethyldimethoxysilane, 2-methacryloyloxyethyltrimethoxysilane, 3-acryloyloxypropylmethyldimethoxysilane, 2-acryloyloxyethyltrimethoxysilane, 2-methacryloyloxyethyltriethoxysilane, 3-acryloyloxypropyltrimethoxysilane, 3-acryloyloxypropyltripropoxysilane, 3-methacryloyloxypropyltriethoxysilane, 3-methacryloyloxypropyltriacetoxysilane, 3-methacryloyloxypropylmethyldimethoxysilane, vinyltrichlorosilane, vinyltrimethoxysilane (GENIOSIL XL 10), vinyltris(2-methoxyethoxy)silane (GENIOSIL GF 58), vinyltriacetoxysilane or mixtures thereof. Preference is given to using, as organofunctional silanes, 3-methacryloyloxypropyltrimethoxysilane (Dynasylan MEMO, Silquest A-174NT), vinyltri(m)ethoxysilane (Dynasylan VTMO and VTEO, Silquest A-151 and A-171), methyltri(m)ethoxysilane (Dynasylan MTMS and MTES), beta-(3,4-epoxycyclohexyl)ethyltrimethoxysilane (Silquest A-186), bis(triethoxysilyl)ethane (Silquest Y-9805), gamma-isocyanatopropyltrimethoxysilane (Silquest A-Link 35, GENIOSIL GF40), methacryloyloxymethyltri(m)ethoxysilane (GENIOSIL XL 33, XL 36), (methacryloyloxymethyl)(m)ethyldimethoxysilane (GENIOSIL XL 32, XL 34), 3-(triethoxysilyl)propylsuccinic anhydride (GENIOSIL GF 20), vinyltrimethoxysilane (GENIOSIL XL 10) and/or vinyltris(2-methoxyethoxy)silane (GENIOSIL GF 58).

It is also possible to apply other organofunctional silanes to the particles of the invention or the pigments of the invention.

In addition, it is possible to use aqueous prehydrolyzates commercially available, for example, from Degussa. These include aqueous aminosiloxane (Dynasylan Hydrosil 1151), aqueous amino-/alkyl-functional siloxane (Dynasylan Hydrosil 2627 or 2909), aqueous diamino-functional siloxane (Dynasylan Hydrosil 2776), aqueous epoxy-functional siloxane (Dynasylan Hydrosil 2926), amino-/alkyl-functional oligosiloxane (Dynasylan 1146), vinyl-/alkyl-functional oligosiloxane (Dynasylan 6598), oligomeric vinylsilane (Dynasylan 6490) or oligomeric short-chain alkyl-functional silane (Dynasylan 9896).

In a preferred embodiment, the organofunctional silane mixture, as well as at least one silane without a functional bonding group, comprises at least one amino-functional silane. The amino function is a functional group which can enter into one or more chemical interactions with most of the groups present in binders. This may include a covalent bond, for example with isocyanate or carboxylate functions of the binder, or hydrogen bonds such as with OH or COOR functions, or else ionic interactions. An amino function is therefore of very good suitability for the purpose of chemical attachment of the pigment to various kinds of binder.

Preference is given to taking the following compounds for this purpose: 3-aminopropyltrimethoxysilane (Dynasylan AMMO; Silquest A-1110), 3-aminopropyltriethoxysilane (Dynasylan AMEO), [3-(2-aminoethyl)aminopropyl]trimethoxysilane (Dynasylan DAMO, Silquest A-1120), [3-(2-aminoethyl)aminopropyl]triethoxysilane, triamino-functional trimethoxysilane (Silquest A-1130), bis(gamma-trimethoxysilylpropyl)amine (Silquest A-1170), N-ethyl-gamma-aminoisobutyltrimethoxysilane (Silquest A-Link 15), N-phenyl-gamma-aminopropyltrimethoxysilane (Silquest Y-9669), 4-amino-3,3-dimethylbutyltrimethoxysilane (Silquest A-1637), ((cyclohexylamino)methyl)(diethoxy)methylsilane (GENIOSIL XL 924), N-cyclohexylaminomethyltriethoxysilane (GENIOSIL XL 926), N-(phenylaminomethyl)trimethoxysilane (GENIOSIL XL 973) or mixtures thereof.

In a preferred embodiment, the optionally present protective layer has the composition disclosed in the respective main claims of WO 2006/021386 A1, WO 2012/130897 A1 or WO 2014/053454 A1.

In addition, the absorbent effect pigments of the invention may have been provided with a surface modification which, for example, facilitates the incorporation of the effect pigments into different media. In the case of use of the absorbent effect pigments of the invention in powder coatings, for example, the effect pigments preferably have one of the surface modifications disclosed in the main claims of EP 2 698 403 A1 or of EP 2 576 702 A1. Alternatively, the absorbent effect pigments of the invention may also have an outermost coating according to WO 2006/136435 A2, claim 32, which is preferably applied by the spray drying method according to WO 2006/136435 A2, claim 1.

In the case of use of the absorbent effect pigments of the invention in cosmetic formulations, the incorporation thereof into O/W, W/O or W/Si emulsion systems, for example, can be facilitated by hydrophobic surface coverage, for example with triethoxycaprylylsilane, and more prolonged emulsion stability can be achieved.

The absorbent effect pigments of the invention can also be used in mixtures with transparent and/or hiding (in)organic white, chromatic or black pigments and/or metal effect pigments and/or pearlescent pigments and/or fillers in the application desired in each case. The amount in which the absorbent effect pigments of the invention are used depends on the particular application and on the optical effect to be achieved.

The absorbent effect pigments of the invention can be used in cosmetic formulations, plastics, films, textiles, ceramic materials, glasses, paints, printing inks, writing inks, lacquers and powder coatings. In addition, the absorbent effect pigments of the invention can also be used for functional applications, for example laser marking, greenhouse films or agricultural films.

In cosmetic formulations, for example body powder, face powder, pressed or loose powder, powder cream, eye makeup such as eyeshadow, mascara, eyeliner, liquid eyeliner, eyebrow pencil, lip balm, lipstick, lip gloss, lip liner, hair styling compositions such as hair spray, hair mousse, hair gel, hair wax, hair mascara, permanent or semipermanent hair dyes, temporary hair dyes, skincare compositions such as lotions, gels, emulsions, nail varnish compositions, it is possible to combine the absorbent effect pigments of the invention with raw materials, auxiliaries and active ingredients suitable for the particular application. The total concentration of absorbent effect pigments of the invention in the cosmetic formulation may be between 0.001% by weight for rinse-off products and 40.0% by weight for leave-on products, based in each case on the total weight of the formulation.

In a further embodiment, the absorbent effect pigments of the invention may be in compact particulate form. Compact particulate form is understood to mean pellets in the form of preferably cylinders and/or beads. The cylinders here preferably have a diameter from a range from 0.2 cm to 4.2 cm, more preferably from a range from 0.5 cm to 2.3 cm and most preferably from a range from 0.7 cm to 1.7 cm, and preferably a length from a range from 0.2 cm to 7.1 cm, more preferably from a range from 0.6 cm to 5.3 cm and most preferably from a range from 0.8 cm to 3.7 cm. The beads preferably have a radius of 1 cm, more preferably from a range from 0.2 cm to 0.7 cm and most preferably from a range from 0.3 cm to 0.5 cm.

In a further embodiment, the present invention relates to an absorbent effect pigment comprising a nonmetallic substrate in platelet form, preferably a synthetic mica platelet or a glass platelet, and a coating applied thereto, wherein the coating comprises
a) optionally a layer 1 comprising or consisting of tin oxide, tin hydroxide and/or tin oxide hydrate,
b) a layer 2 comprising at least one metal oxide, metal hydroxide and/or metal oxide hydrate, where the metal ion comprises or is at least one metal ion selected from the group of metals consisting of Ti, Sn and Fe,
c) a layer 3 comprising at least one metal oxide, metal hydroxide and/or metal oxide hydrate, where the metal ion comprises or is at least one metal ion selected from the group of metals consisting of Ti, Sn, Ce and Fe,
where at least one of layers 2 and 3 comprises at least two different metal ions from the groups listed above, where the proportion of coloring metal ions, determined in each case via XRF and calculated in each case as the elemental metal, is within a range from 7.5% by weight to 75% by weight, based on the total weight of the effect pigment, layers 2 and 3 are interrupted by a spacer layer of mean height $h_a$ from a range from 10 nm to 66 nm, the standard deviation of the relative height $h_{Rma}$ is within a range from 0.2% to 11%, and the network density is within a range from 1% to 79%.

In a further embodiment, the present invention relates to an absorbent effect pigment comprising a nonmetallic substrate in platelet form, preferably a synthetic mica platelet or a glass platelet, and a coating applied thereto, wherein the coating comprises
a) optionally a layer 1 comprising or consisting of tin oxide, tin hydroxide and/or tin oxide hydrate,
b) a layer 2 comprising at least one metal oxide, metal hydroxide and/or metal oxide hydrate, where the metal ion comprises or is at least one noncoloring metal ion selected from the group of metals consisting of Fe, Ti, Sn and Zr,
c) a layer 3 comprising at least one metal oxide, metal hydroxide and/or metal oxide hydrate, where the metal ion comprises or is at least one noncoloring metal ion selected from the group of metals consisting of Fe, Ti, Sn and Zr,
and at least one of layers 2 and 3 comprises at least two different metal ions from the groups listed above, layers 2 and 3 are interrupted by a spacer layer, and where the effect pigments have a span $\Delta D$ from a range from 0.8 to 1.9.

In a preferred embodiment, the present invention relates to an absorbent effect pigment comprising a nonmetallic substrate in platelet form, preferably a synthetic mica platelet or a glass platelet, and a coating applied thereto, wherein the coating comprises
a) optionally a layer 1 comprising or consisting of tin oxide, tin hydroxide and/or tin oxide hydrate,
a) a layer 2 comprising at least one metal oxide, metal hydroxide and/or metal oxide hydrate composed of or comprising at least one metal ion selected from the group of metals consisting of Ti, Fe, Sn and Zr,
b) a layer 3 comprising at least one metal oxide, metal hydroxide and/or metal oxide hydrate composed of or comprising at least one metal ion selected from the group of metals consisting of Ti, Fe, Sn and Zr,
and at least one of layers 2 and 3 comprises at least two different metal ions from the groups listed above, where the proportion of coloring metal ions, determined in each case via XRF and calculated in each case as the elemental metal, is within a range from 4.0% by weight to 79% by weight in total, preferably within a range from 5.0% by weight to 72% by weight, based in each case on the total weight of the effect pigment, layers 2 and 3 are interrupted by a spacer layer and the effect pigment has a chemical resistance with a dE of <3, preferably <2.

In a particularly preferred embodiment, the present invention relates to an absorbent effect pigment comprising a nonmetallic substrate in platelet form, preferably a synthetic mica platelet or a glass platelet, and a coating applied thereto, wherein the coating comprises
a) optionally a layer 1 comprising or consisting of tin oxide, tin hydroxide and/or tin oxide hydrate,
b) a layer 2 comprising at least one metal oxide, metal hydroxide and/or metal oxide hydrate, where the metal ions comprise or are at least two metal ions selected from the group of metals consisting of Fe and Sn,
c) a layer 3 comprising at least one metal oxide, metal hydroxide and/or metal oxide hydrate, where the metal ions comprise or are at least two metal ions selected from the group of metals consisting of Fe and Sn,
and layers 2 and 3 are interrupted by a spacer layer, where the coating comprises further layers of high and/or low refractive index and the effect pigment comprises at least one further spacer layer which runs essentially parallel to the surface of the nonmetallic substrate in platelet form and is of mean height $h_a$ from a range from 11 nm to 76 nm, preferably from a range from 19 nm to 54 nm.

In a further embodiment, the present invention relates to an absorbent effect pigment comprising a nonmetallic substrate in platelet form, preferably a synthetic mica platelet or a glass platelet, and a coating applied thereto, wherein the coating comprises
a) optionally a layer 1 comprising or consisting of tin oxide, tin hydroxide and/or tin oxide hydrate,
b) a layer 2 comprising at least one metal oxide, metal hydroxide and/or metal oxide hydrate, where the metal ion comprises or is at least one metal ion selected from the group of metals consisting of Zr, Sn and Fe,
c) a layer 3 comprising at least one metal oxide, metal hydroxide and/or metal oxide hydrate, where the metal ion comprises or is at least one metal ion selected from the group of metals consisting of Zr, Sn, Ce and Fe,
where at least one of the layers 2 and 3 comprises at least two different metal ions from the groups listed above, the quotient of the mean layer thickness of layer 2 and the mean layer thickness of layer 3 is preferably within a range from 0.5 to 1.8, and the standard deviation of the relative height $h_{Rma}$ is within a range from 0.2% to 11%.

In a further embodiment, the absorbent effect pigments of the invention have a hue angle $h^*_{15}$ within the CIE LCh color space from a range from 0° to 60° and 120° to 360°, further preferably from a range from 0° to 45° and 135° to 360°, more preferably from a range from 0° to 35° and 140° to 360°, and most preferably from a range from 0° to 30° and 145° to 360°. Preferably, the chroma C*15 within the aforementioned hue angle ranges is >15, more preferably >20 and most preferably >30. The hue angle $h^*_{15}$ and the chroma $C^*_{15}$ are determined here using lacquer applications, on black/white hiding charts (Byko-Chart 2853, from Byk-Gardner), of a nitrocellulose lacquer (Erco 2615e bronze-mixing lacquer colorless; from Maeder Plastiklack AG) which has been admixed with 6% by weight of the particular effect pigment of the invention, according to the details which follow in section IIb "Angle-dependent color measurements".

The CIE LCh color space is the CIELab color space, wherein the cylinder coordinates C* (chroma, relative color saturation, distance from the L axis) and h* (hue angle, angle of the hue in the CIELab color circle) are reported rather than the Cartesian coordinates a*, b*.

In a further embodiment, the present invention relates to an absorbent effect pigment comprising a nonmetallic substrate in platelet form, preferably a synthetic mica platelet or a glass platelet, and a coating applied thereto, where the coating has through at least one spacer layer essentially parallel to the surface of the nonmetallic substrate in platelet form and the effect pigment is obtainable by i) optionally applying an uncalcined tin oxide, tin hydroxide and/or tin oxide hydrate layer to the nonmetallic substrate in platelet form, ii) applying three uncalcined metal oxides, metal hydroxides and/or metal oxide hydrates, where the second of these uncalcined metal oxides, metal hydroxides and/or metal oxide hydrates is physically different from the others and is of such a nature that it can diffuse into at least one of the other uncalcined metal oxides, metal hydroxides and/or metal oxide hydrates, and iii) calcining the product obtained in step ii), optionally under reducing conditions, at a temperature from a range from 400° C. to 980° C.

In a very particularly preferred embodiment, the present invention relates to an absorbent effect pigment comprising a nonmetallic substrate in platelet form, preferably a synthetic mica platelet or a glass platelet, and a coating applied thereto, where the coating has at least one spacer layer which is essentially parallel to the surface of the nonmetallic substrate in platelet form and is of mean height $h_a$ from a range from 14 nm to 51 nm, and the effect pigment is obtainable by i) optionally applying an uncalcined tin oxide, tin hydroxide and/or tin oxide hydrate layer using a water-soluble tin(IV) salt to the nonmetallic substrate in platelet form, ii) sequentially applying a first layer A using a water-soluble iron(III) salt, a second layer B using a water-soluble tin(IV) salt and/or titanium(IV) salt, a third layer C using a water-soluble iron(III) salt, and iii) calcining the product obtained in step ii) at a temperature from a range from 400° C. to 910° C.

In a preferred embodiment, the coating of the absorbent effect pigments of the invention, in each case prior to drying and/or calcination, comprises at least one layer of high refractive index composed of or comprising titanium oxide, titanium hydroxide and/or titanium oxide hydrate and at least two nonadjacent layers of high refractive index composed of or comprising iron oxide, iron hydroxide and/or iron oxide hydrate, where the weight ratio in the effect pigment of titanium to iron is <1, preferably within a range from 0.01 to 0.9 and more preferably within a range from 0.1 to 0.8.

In a further-preferred embodiment, the coating of the absorbent effect pigments of the invention, in each case prior to drying and/or calcination, comprises at least one layer of high refractive index composed of or comprising tin oxide, tin hydroxide and/or tin oxide hydrate and at least two layers of high refractive index composed of or comprising iron oxide, iron hydroxide and/or iron oxide hydrate, where the weight ratio in the effect pigment of tin to iron is <1, preferably within a range from 0.01 to 0.9 and more preferably within a range from 0.1 to 0.8. In this embodiment, it is especially preferable that first at least one high-refractive index layer of iron oxide, iron hydroxide and/or iron oxide hydrate and then at least one high-refractive index layer of tin oxide, tin hydroxide and/or tin oxide hydrate and a further high-refractive index layer of iron oxide, iron hydroxide and/or iron oxide hydrate are applied directly to the substrate in platelet form or directly to the respective uppermost layer close to the substrate. In addition, it is also possible, prior to application of the at least one high-refractive index layer of iron oxide, iron hydroxide, iron oxide hydrate, to deposit a layer or preliminary coverage with metal oxides, metal hydroxides, metal oxide hydrates, where the metal ion comprises or is a metal ion selected from the group of metals consisting of Sn and Si, directly to the nonmetallic substrate in platelet form or directly to the respective uppermost layer close to the substrate, where the layer thickness may be a few nanometers, preferably less than 10 nm, more preferably less than 5 nm and most preferably less than 3 nm, and said layer need not fully surround the substrate. The tin oxide, tin hydroxide and/or tin oxide hydrate may be present at least partly in a mixed layer with the iron oxide, iron hydroxide and/or iron oxide hydrate.

In a further preferred embodiment, the coating of the absorbent effect pigments of the invention, in each case prior to drying and/or calcination, comprises at least one high-refractive index layer of iron oxide, iron hydroxide and/or iron oxide hydrate, where at least one further layer of tin oxide, tin hydroxide and/or tin oxide hydrate has been applied to this at least one layer in a proportion from a range from 1% by weight to 25% by weight, preferably from a range from 2% by weight to 20% by weight, more preferably from a range from 3% by weight to 16% by weight and most preferably from a range from 4% by weight to 13% by weight, based in each case on the absorbent effect pigment. Alternatively, the at least one high-refractive index layer of iron oxide, iron hydroxide and/or iron oxide hydrate may have been doped with Mg or Ce. After calcination, iron oxide present in the coating may be present in the form of hematite and/or goethite.

In a further embodiment, the present invention relates to an absorbent effect pigment comprising a nonmetallic substrate in platelet form, preferably a synthetic mica platelet or a glass platelet, and a coating applied to the substrate, where the coating has at least one spacer layer essentially parallel to the surface of the nonmetallic substrate in platelet form and the effect pigment has been calcined under reducing conditions or has a semitransparent metal layer in the overall coating, preferably as the outermost layer directly beneath an optionally present protective layer.

In one embodiment, the coating of the absorbent effect pigments of the invention, rather than the at least one metal oxide, metal hydroxide and/or metal oxide hydrate, comprises the corresponding metal suboxides, metal fluorides, metal nitrides, metal oxynitrides, metal oxyhalides and/or metal sulfides.

In one embodiment, the coating of the absorbent effect pigments of the invention comprises, in addition to the at least one metal oxide, metal hydroxide and/or metal oxide hydrate, at least one metal suboxide, metal fluoride, metal nitride, metal oxynitride, metal oxyhalide and/or metal sulfide.

There follows an elucidation of the invention by a few examples, but the examples do not restrict the invention. All % figures in the examples and comparative examples should be understood as % by weight.

I PRODUCTION OF THE ABSORBENT EFFECT PIGMENTS OF THE INVENTION

Example 1

200 g of synthetic mica platelets (fluorphlogopite platelets) having a particle size distribution according to MALVERN Mastersizer MS 2000: $D_{10}$=10 µm, $D_{50}$=22 µm, $D_{90}$=40 µm were suspended in 1300 mL of demineralized water and heated to 85° C. with turbulent stirring. The pH of the suspension was lowered to pH 2.2. By addition of 75 g of a tin chloride solution of concentration c(Sn)=12 g/L, a layer of tin oxide was deposited on the surface of the glass platelets.

The pH of the suspension was subsequently lowered to pH 1.9 and then a solution of 570 mL of $TiCl_4$ (200 g of $TiO_2$/L of demineralized water) was dosed into the suspension. After the end of the addition, the mixture was stirred for a further 10 minutes and then the pH was adjusted to pH 2.6. Subsequently, 50 mL of an aqueous iron chloride solution having a density of 1.42 g/cm$^3$ were dosed. On completion of dosage, the mixture was stirred for another 10 minutes, the pH was adjusted to pH 1.9, and 630 mL of a solution of $TiCl_4$ (200 g of $TiO_2$/L of demineralized water) were dosed into the suspension.

Thereafter, a further dosage of 40 mL of an aqueous iron chloride solution having a density of 1.42 g/cm$^3$ was added in after 10 minutes. 15 minutes after the addition had ended, the suspension was filtered off and the filtercake was washed. The filtercake was dried and calcined at 850° C. for 60 min. Extremely chromatic, high-gloss gold interfering effect pigments with yellow absorption color and very good hiding capacity were obtained.

Example 2

The filtercake from example 1 was dried and calcined at 820° C. for 60 minutes under a hydrogen atmosphere. Highly chromatic, high-gloss green/gold interference effect pigments with black absorption color and good hiding capacity were obtained.

Example 3

200 g of synthetic mica platelets (fluorphlogopite platelets) having a particle size distribution according to MALVERN Mastersizer MS 2000: $D_{10}$=10 µm, $D_{50}$=22 µm, $D_{90}$=40 µm were suspended in 1300 mL of demineralized water and heated to 85° C. with turbulent stirring. The pH of the suspension was lowered to pH 2.2. By addition of 100 g of a tin chloride solution of concentration c(Sn)=12 g/L, a layer of tin oxide was deposited on the surface of the synthetic mica platelets.

The pH of the suspension was lowered to pH 1.9 and then a solution of 400 mL of $TiCl_4$ (200 g of $TiO_2$/L of demineralized water) was dosed into the suspension. After the end of the addition, the mixture was stirred for a further 10 minutes and then the pH was adjusted to pH 2.6. Subsequently, 30 mL of an aqueous iron chloride solution having a density of 1.42 g/cm$^3$ were dosed in. On completion of addition, the mixture was stirred for another 10 minutes, and 405 mL of a further solution of $TiCl_4$ (200 g of $TiO_2$/L of demineralized water) were dosed into the suspension. Thereafter, a further dosage of 40 mL of an aqueous iron chloride solution having a density of 1.42 g/cm$^3$ was added after 10 minutes. 15 minutes after the addition had ended, the suspension was filtered off and the filtercake was washed. The filtercake was dried and calcined at 650° C. for 30 minutes under reducing conditions. Highly chromatic, glossy blue interfering effect pigments with gray absorption color were obtained.

Example 4

200 g of glass platelets having a particle size distribution according to MALVERN Mastersizer MS 2000: $D_{10}$=34 µm, $D_{50}$=57 µm, $D_{90}$=96 µm were suspended in 1300 mL of DM water (DM=demineralized) and heated to 85° C. with turbulent stirring. The pH of the suspension was lowered to pH 2.2. By addition of 75 g of a tin chloride solution of concentration c(Sn)=12 g/L, a layer of tin oxide was deposited on the surface of the glass platelets.

Thereafter, the pH was lowered to pH 2.0 with dilute HCl, and then a solution of 148 mL of $TiCl_4$ (200 g of $TiO_2$/L of demineralized water) was dosed into the suspension. After the end of the addition, the mixture was stirred for a further 10 minutes and then the pH was adjusted to pH 2.6. Subsequently, 8 mL of an aqueous iron chloride solution having a density of 1.25 g/cm$^3$ were dosed in. On completion of dosage, the mixture was stirred for another 10 minutes and, by addition of 75 mL of tin chloride solution of concentration c(Sn)=12 g/L, a further thin layer of tin oxide was deposited on the pigment surface. Subsequently, 180 mL of a solution of $TiCl_4$ (200 g of $TiO_2$/L of demineralized water) were doesd into the suspension. Thereafter, 20 mL of an aqueous iron chloride solution having a density of 1.25 g/cm$^3$ were dosed in after 10 minutes. 15 minutes after the addition, the suspension was filtered off and the filtercake was washed. The filtercake was dried and calcined at 750° C. for 60 minutes under reducing conditions. Extremely chromatic, high-gloss gold interfering effect pigments with gray absorption color were obtained.

Example 5

200 g of synthetic mica platelets (fluorphlogopite platelets) having a particle size distribution according to MALVERN Mastersizer MS 2000: $D_{10}$=10 µm, $D_{50}$=22 µm, $D_{90}$=40 µm were suspended in 1300 mL of demineralized water and heated to 85° C. with turbulent stirring. The pH of the suspension was lowered to pH 2.6.

Subsequently, 40 mL of an aqueous iron chloride solution having a density of 1.42 g/cm$^3$ was dosed in. Thereafter, the mixture was stirred for 10 minutes and, at pH 1.9, 560 mL of a solution of $TiCl_4$ (200 g of $TiO_2$/L of demineralized water) were dosed into the suspension.

After adjusting the pH to the initial value, 40 mL of an aqueous iron chloride solution having a density of 1.42 g/cm$^3$ were then added to the suspension. Once more, the pH was adjusted to pH 1.9 and 600 mL of a solution of $TiCl_4$ (200 g of TiO$_2$/L of demineralized water) were dosed into the suspension. A further addition of 15 mL of an aqueous iron chloride solution having a density of 1.42 g/cm$^3$ was executed and then the mixture was stirred for a further 120 min and filtered. The washed filtercake was dried and calcined at 800° C. for 45 min. Extremely chromatic, high-gloss gold interfering effect pigments with yellow absorption color and very good hiding capacity were obtained.

Example 6

200 g of synthetic mica platelets (fluorphlogopite platelets) having a particle size distribution according to MALVERN Mastersizer MS 2000: D$_{10}$=10 µm, D$_{50}$=22 µm, D$_{90}$=40 µm were suspended in 1300 mL of demineralized water and heated to 85° C. with turbulent stirring. The pH of the suspension was adjusted to pH 2.6. By addition of 500 g of an aqueous iron chloride solution having a density of 1.42 g/cm$^3$, a layer of iron oxide was deposited on the surface of the synthetic mica platelets.

After the end of the addition, the mixture was stirred for a further 120 minutes and then the pH was adjusted to pH 2.2. Subsequently, 1000 g of a tin chloride solution of concentration c(Sn)=12 g/L were dosed in. On completion of dosage, the mixture was stirred for another 120 minutes and then, by addition of 710 g of an aqueous iron chloride solution having a density of 1.42 g/cm$^3$, a further layer of iron oxide was deposited on the surface of the synthetic mica platelets. 60 minutes after the addition had ended, the suspension was filtered off and the filtercake was washed. The filtercake was dried if appropriate and calcined at 800° C. for 60 minutes under reducing conditions. Extremely chromatic, high-gloss red interfering effect pigments with red absorption color and with very good hiding power were obtained.

Example 7

200 g of synthetic mica platelets (fluorphlogopite platelets) having a particle size distribution according to MALVERN Mastersizer MS 2000: D$_{10}$=10 µm, D$_{50}$=22 µm, D$_{90}$=40 µm were suspended in 1300 mL of demineralized water and heated to 85° C. with turbulent stirring. The pH of the suspension was adjusted to pH 2.2. By addition of 100 g of a tin chloride solution of concentration c(Sn)=12 g/L, a layer of tin oxide was deposited on the surface of the synthetic mica platelets.

The pH of the suspension was lowered thereafter to pH 1.9 and then a solution of 400 mL of TiCl$_4$ (200 g of TiO$_2$/L of demineralized water) was dosed into the suspension. After the end of the addition, the mixture was stirred for a further 10 minutes and then the pH was adjusted to pH 2.2. Subsequently, 150 mL of a 20% by weight aqueous zirconium chloride solution were dosed in. On completion of metered addition, the mixture was stirred for a further 40 minutes, and 300 mL of TiCl$_4$ (200 g of TiO$_2$/L of demineralized water) were dosed into the suspension. After the addition had ended, the suspension was filtered off and the filtercake was washed. The filtercake was dried and calcined at 800° C. for 60 minutes under reducing conditions. Highly chromatic, highly glossy blue interfering effect pigments with gray absorption color were obtained.

Example 8

15 g of pigment from example 6 were suspended in 450 mL of demineralized water. Thereafter, 30 mL of silver salt solution consisting of 50 g of AgNO$_3$ and 50 mL of 28% by weight ammonia solution were supplemented up to 1 L with demineralized water, and the suspension was added simultaneously and stirred at room temperature for 5 minutes. Subsequently, 9 mL of a 35% by weight formaldehyde solution were added and the mixture was stirred for a further 1 hour. The suspension was then filtered and the pigment cake was dried at 120° C. under reduced pressure.

Dark blue interfering effect pigments with black absorption color and a silver content of 11.1% were obtained.

Example 9

100 g of the effect pigment obtained from example 1 were suspended in 850 mL of demineralized water and heated to 85° C. with turbulent stirring. The pH was lowered to pH 4.2 with dilute hydrochloric acid. Then a solution of 0.93 g of Ce(NO$_3$)$_3$×6 H$_2$O dissolved in 40 mL of demineralized water was metered in. At the same time, the pH was kept constant by dropwise addition of a 10% NaOH solution. Once the solution had been added completely, the mixture was stirred for a further hour and the pH was adjusted thereafter to pH 10 with dilute sodium hydroxide solution. Thereafter, 5.7 g of Dynasylan 1146 diluted with 24.3 g of demineralized water were added to the suspension, the suspension was stirred for another 180 minutes and filtered, and the filtercake was washed with demineralized water. The filtercake was dried at 95° C. under reduced pressure.

Example 10

200 g of synthetic mica platelets (fluorphlogopite platelets) having a particle size distribution according to MALVERN Mastersizer MS 2000: D$_{10}$=10 µm, D$_{50}$=22 µm, D$_{90}$=40 µm were suspended in 1300 mL of demineralized water and heated to 85° C. with turbulent stirring. The pH of the suspension was adjusted to pH 2.6. By addition of 570 g of an aqueous iron chloride solution having a density of 1.42 g/cm$^3$, a layer of iron oxide was deposited on the surface of the synthetic mica platelets.

The pH of the suspension was lowered thereafter to pH 1.9 and then a solution of 250 mL of TiCl$_4$ (200 g of TiO$_2$/L of demineralized water) was dosed into the suspension.

Thereafter, the mixture was stirred for another 120 minutes and then, by addition of 600 g of an aqueous iron chloride solution having a density of 1.42 g/cm$^3$, a further layer of iron oxide was deposited on the surface of the synthetic mica platelets. 60 minutes after the addition had ended, the suspension was filtered off and the filtercake was washed. The filtercake was dried if necessary and calcined at 400° C. for 60 minutes. Extremely chromatic, high-gloss red interfering effect pigments with red absorption color and very good hiding power were obtained.

Example 11

100 g of the effect pigment obtained from example 6 were suspended in 850 mL of demineralized water and heated to 85° C. with turbulent stirring. The pH was lowered to pH 4.2 with dilute hydrochloric acid. Then a solution of 0.93 g of Ce(NO$_3$)$_3$×6 H$_2$O dissolved in 40 mL of demineralized water was dosed in. At the same time, the pH was kept constant by dropwise addition of a 10% NaOH solution. Once the solution had been added completely, the mixture was stirred for a further hour and the pH was adjusted thereafter to pH 10 with dilute sodium hydroxide solution. Thereafter, 5.7 g of Dynasylan 1146 diluted with 24.3 g of demineralized water were added to the suspension, the suspension was stirred for another 180 minutes and filtered, and the filtercake was washed with demineralized water. The filtercake was dried at 95° C. under reduced pressure.

Example 12

300 g of glass platelets having a particle size distribution according to MALVERN Mastersizer MS 2000: $D_{10}$=10 µm, $D_{50}$=20 µm, $D_{90}$=40 µm were suspended in 1500 mL of demineralized water and heated to 85° C. with turbulent stirring. The pH of the suspension was lowered to pH 2.2. By addition of 70 mL of a tin chloride solution of concentration c(Sn)=12 g/L, a layer of tin oxide was deposited on the surface of the glass platelets. Thereafter, the pH was lowered to pH 2.0 with dilute HCl, and then a solution of 250 mL of $TiCl_4$ (200 g of $TiO_2$/L of demineralized water) was dosed into the suspension. After the end of the addition, the mixture was stirred for a further 10 minutes and then the pH was adjusted to pH 2.6. Subsequently, 100 mL of an aqueous iron chloride solution having a density of 1.25 $g/cm^3$ were dosed in. Subsequently, 300 mL of a solution of $TiCl_4$ (200 g of $TiO_2$/L of demineralized water) were dosed into the suspension. 15 minutes after completion of addition, the suspension was filtered off and the filtercake was washed. The filtercake was dried and calcined at 760° C. for 60 minutes. Extremely chromatic, high-gloss golden effect pigments were obtained.

Comparative Example 1

200 g of synthetic mica platelets (fluorphlogopite platelets) having a particle size distribution according to MALVERN Mastersizer MS 2000: $D_{10}$=25 µm, $D_{50}$=55 µm, $D_{50}$=100 µm, span ΔD=1.36 were suspended in 1300 mL of DM water (DM=demineralized) and heated to 85° C. with stirring. The pH of the suspension was lowered to pH 2.2. By addition of 100 g of a tin chloride solution of concentration c(Sn)=12 g/L, a layer of "$SnO_2$" was deposited on the surface of the synthetic mica platelets. Thereafter, the pH was lowered to pH 1.9 with dilute HCl, and then a solution of 500 mL of $TiCl_4$ (200 g of $TiO_2$/L of demineralized water) was metered into the suspension. After the end of the addition, the mixture was stirred for a further 10 minutes and then the pH were adjusted to pH 2.6. Subsequently, 60 mL of an aqueous iron chloride solution having a density of 1.42 $g/cm^3$ was metered in. 15 minutes after completion of addition, the suspension was filtered off and the filtercake was washed. The filtercake was dried and calcined at 700° C. for 60 minutes under reducing conditions. Shiny gold pigments with dark absorption color were obtained.

Comparative Example 2

Red effect pigment based on natural mica platelets, coated with iron oxide, Iriodin 504 Red, from Merck.

Comparative Example 3

Red effect pigment based on $SiO_2$ platelets, coated with iron oxide, Iriodin 4504 Lava Red, from Merck.

II CHARACTERIZATION OF THE ABSORBENT EFFECT PIGMENTS AND PIGMENTS FROM THE COMPARATIVE EXAMPLES

IIa Particle Size Measurement

The size distribution curve of the absorbent effect pigments of the invention and of the pigments from the comparative examples was determined using the Malvern Mastersizer 2000 instrument according to the manufacturer's instructions. For this purpose, about 0.1 g of the respective pigment was introduced into the sample preparation cell of the measuring instrument by means of a Pasteur pipette as an aqueous solution, without addition of dispersing aids, with constant stirring, and analyzed repeatedly. The individual measurement results were used to form the medians. The scattered light signals were evaluated by the Fraunhofer method.

The median particle size $D_{50}$ in the context of this invention is understood to mean the $D_{50}$ of the cumulative frequency distribution of the volume-averaged size distribution function, as obtained by laser diffraction methods. The $D_{50}$ indicates that 50% of the pigments have a diameter equal to or less than the value reported, for example 20 µm. Correspondingly, the $D_{10}$ and $D_{90}$ respectively state that 10% and 90% of the pigments have a diameter equal to or less than the respective measured value. The span ΔD, defined as $\Delta D = D_{90} - D_{10}/D_{50}$, indicates the breadth of the particle size distribution. With regard to the visual appearance of the absorbent effect pigments of the invention, a small value of ΔD, i.e. a narrow span, is preferred.

TABLE 2

Particle sizes

| Example/comparative example | $D_{10}$ [µm] | $D_{50}$ [µm] | $D_{90}$ [µm] | Span |
|---|---|---|---|---|
| Example 1 | 10.8 | 22.5 | 40.6 | 1.326 |
| Example 2 | 11.0 | 22.8 | 40.8 | 1.307 |
| Example 3 | 12.4 | 23.7 | 42.1 | 1.254 |
| Example 4 | 28.1 | 53.0 | 92.7 | 1.219 |
| Example 5 | 11.9 | 22.9 | 40.9 | 1.271 |
| Example 6 | 12.5 | 23.0 | 40.4 | 1.217 |
| Example 7 | 11.9 | 22.4 | 39.9 | 1.247 |
| Example 8 | 13.7 | 24.3 | 41.3 | 1.138 |
| Example 9 | 11.1 | 22.6 | 40.8 | 1.314 |
| Example 10 | 8.8 | 20.1 | 37.6 | 1.429 |
| Example 12 | 9.7 | 21.3 | 41.3 | 1.482 |
| Comparative example 1 | 12.0 | 22.9 | 40.8 | 1.260 |
| Comparative example 2 | 10.8 | 21.9 | 41.5 | 1.402 |
| Comparative example 3 | 9.7 | 19.3 | 35.5 | 1.337 |

IIb Angle-Dependent Color Measurements

To measure the color and brightness values, the effect pigments of the invention and the pigments from the comparative examples were stirred into a conventional nitrocellulose lacquer (Erco 2615e bronze mixing lacquer colorless; from Maeder Plastiklack AG) at a pigmentation level of 6% by weight, based on the total weight of the wet lacquer. This was done by initially charging the respective pigments and then dispersing them into the lacquer with a brush. The finished lacquer was applied to black/white hiding charts (Byko-Chart 2853, from Byk-Gardner) in a wet film thickness of 40 µm or of 76 µm (example 4) with a spiral applicator on an applicator drawdown apparatus (RK Print Coat Instr. Ltd. Citenco K 101 drawdown apparatus), and subsequently dried at room temperature. The choice of spiral applicator is made according to table A depending on the $D_{50}$ of the pigments or substrates to be applied in each case.

The BYK-mac multi-angle colorimeter (from Byk-Gardner) was used to determine the color values on the black background of the hiding chart at a constant angle of incidence of 45° (according to the manufacturer's instructions) at various observation angles relative to the specular angle. Characterization of the color intensity was accomplished using the chroma value C*15, which was measured at a measurement angle separated by 15° from the specular angle on the black background of the black/white hiding chart.

Strongly reflecting samples (mirrors in the ideal case) reflect virtually all the incident light at what is called the specular angle. The closer to the specular angle the measurement is made on the lacquer application, the more intense the appearance of the interference color.

TABLE A

Wet film thickness as a function of the $D_{50}$ of the pigments or substrates to be applied

| $D_{50}$ | Spiral applicator |
|---|---|
| <40 μm | 40 μm |
| 40 μm-85 μm | 76 μm |
| >85 μm | 100 μm |

TABLE 3

Color and brightness values of gold effect pigments

| Example/ comparative example | NC lacquer 6% 40 μm BykMac | | | |
|---|---|---|---|---|
| | L 110° s[1] | a*15° s | b*15° s | C* 15° s |
| Example 1 | 91.7 | −7.1 | 46.1 | 46.6 |
| Example 2 | 84.3 | −6.6 | 35.1 | 35.7 |
| Example 4 | 77.4 | −10.6 | 23.3 | 25.6 |
| Example 5 | 90.8 | −10.9 | 38.6 | 40.1 |
| Example 9 | 92.4 | −4.0 | 48.3 | 48.5 |
| Example 12 | 73.74 | −3.50 | 32.84 | 33.02 |
| Comparative example 1 | 83.9 | 1.0 | 25.3 | 25.3 |

TABLE 4

Color and brightness values of red effect pigments

| Example/ comparative example | NC lacquer 6% 40 μm BykMac | | | |
|---|---|---|---|---|
| | L 15° s[1] | a*15° s | b*15° s | C* 15° s |
| Example 6 | 57.8 | 42.3 | 26.8 | 50.0 |
| Example 7 | 72.9 | 16.6 | −29.6 | 34.0 |
| Example 10 | 64.2 | 40.2 | 27.6 | 48.8 |
| Comparative example 2 | 74.5 | 38.6 | 11.4 | 40.2 |

[1]Measured on the black background of the black/white hiding chart.

Table 3 indicates the color values for gold interference effect pigments. It is clear from this that the color intensity of the effect pigments of the invention is much higher than the color intensity of the single-layer pearlescent pigment from comparative example 1. An exception to this is example 4, since this involves a much thicker glass substrate.

The color values for red interference effect pigments that are listed in table 4 for the inventive examples are also well above those of comparative example 2.

IIc Comparison of Hiding

To determine the hiding quotient $D_q$, defined as $$D_q = \frac{L^{*25}_{black}}{L^{*25}_{white}},$$

the brightness values L*25° of the lacquer applications from IIb were recorded with the BYK-mac multi-angle colorimeter (from Byk-Gardner) at a measurement angle of 25° on the black and white backgrounds of the black/white hiding chart. The 25° measurement geometry, at a constant angle of incidence of 45°, relates to the difference from the specular angle. The viewing angle is measured away from the specular reflection in the plane of illumination.

The effect pigments of the invention have good hiding power. The hiding quotient $D_q$ thereof is preferably ≥0.41. The hiding quotient $D_q$ of the inventive absorbent effect pigments in platelet form from examples 1 to 10, as can be inferred from table 5, is in each case well above 0.41.

IId Gloss Measurements

Gloss is a measure of directed reflection. To determine the gloss, the paint applications from IIb on the white background of the black/white hiding chart were analyzed at a measurement angle of 60° based on the vertical with the aid of a Micro-Tri-Gloss gloss meter from Byk-Gardner. The gloss values of the absorbent effect pigments of the invention and of the pigments from the comparative examples are listed in table 5.

Some of the inventive absorbent effect pigments in platelet form from examples 1 to 10 show distinctly higher gloss values than the pigments having a single-layer coating from comparative examples 2 and 3.

The gloss measurements from table 5 confirm the very high reflectivity of the pigments of the invention compared to the prior art.

IIe Effect Measurements

In order to objectively describe the optical effect of the absorbent effect pigments of the invention, effect measurements were conducted with the BYK-mac spectrophotometer (from Byk-Gardner) using the lacquer applications from IIb (cf. Byk-Gardner catalog "Qualitätskontrolle für Lacke and Kunststoffe" [Quality Control for Lacquers and Adhesives], 2011/2012, p. 97/98). The corresponding measurement values for the sparkle intensity S_i, the sparkle area S_a and the graininess G are collected in table 5.

TABLE 5

Effect measurements, hiding quotient and gloss values

| Example/ comparative example | S_i 15° (s)[1] | S_a 15° (s)[1] | G (s)[1] | $D_q$ 25° | 60° gloss (w)[2] |
|---|---|---|---|---|---|
| Example 1 | 15.44 | 33.99 | 9.99 | 0.607 | 85.8 |
| Example 2 | 12.75 | 33.59 | 8.59 | 0.618 | 70.5 |
| Example 3 | 6.14 | 24.72 | 4.66 | 0.495 | 42.3 |
| Example 4 | 53.95 | 33.66 | 13.85 | 0.522 | 81.5 |
| Example 5 | 10.15 | 32.00 | 8.15 | 0.692 | 49.9 |
| Example 6 | 6.16 | 30.01 | 4.37 | 0.558 | 52.6 |
| Example 7 | 5.62 | 24.12 | 5.60 | 0.440 | 40.3 |
| Example 8 | 7.84 | 33.93 | 4.04 | 0.505 | 48.8 |

TABLE 5-continued

Effect measurements, hiding quotient and gloss values

| Example/comparative example | S_i 15° (s)[1] | S_a 15° (s)[1] | G (s)[1] | $D_q$ 25° | 60° gloss (w)[2] |
|---|---|---|---|---|---|
| Example 9 | 14.58 | 33.75 | 9.98 | 0.630 | 90.8 |
| Example 10 | 6.35 | 27.85 | 4.68 | 0.505 | 53.9 |
| Example 12 | 51.65 | 34.71 | 13.17 | 0.4760 | 69.1 |
| Comparative example 2 | 4.70 | 19.38 | 4.15 | 0.661 | 41.8 |
| Comparative example 3 | 4.28 | 18.57 | 3.45 | 0.719 | 32.3 |

[1]Measured on the black background of the black/white hiding chart.
[2]Measured on the white background of the black/white hiding chart.

The effect values S_i, S_a and G of the inventive absorbent effect pigments in platelet form from examples 1 to 10 and 12 are higher than the values for comparative examples 2 and 3. The achievable optical effects of the inventive absorbent effect pigments in platelet form are much more marked than in the case of conventional effect pigments with a single-layer coating from comparative examples 2 and 3.

IIf Waring Blender

In industry, many lacquers are processed in circulation systems. In this case, the lacquer components are subjected to high shear forces. The Waring blender test simulates these conditions and serves for assessment of the ring line stability/shear stability. Specifically pigments wherein the coating has not been adequately anchored on the support material exhibit significant deviations in the chroma values in this test compared to the untreated applications. The Waring blender test can thus be regarded as a measure of the mutual adhesion of the pigment coating with respect to shear forces.

For this purpose, the absorbent effect pigments of the invention or the pigments from the comparative examples were weighed out according to the recipe below and converted stepwise to a paste with a conventional acrylic lacquer in an 880 mL beaker. Thereafter, the viscosity was adjusted with butyl acetate/xylene 1:1 to 17" in the DIN 4 mm cup. A total of 600 g of lacquer were produced, of which 400 g were introduced into a jacketed water-cooled 1 kg vessel and stirred with a specific attachment under the Dispermat (from Waring Blenders). The stirring time was 8 minutes at 13 500 rpm, then 200 g of lacquer were removed and the rest was stirred for a further 12 minutes.
Recipe: 6% pigment
   8% butyl acetate 85
   86% acrylic lacquer, colorless
   30% dilution butyl acetate 85/xylene 1:1
200 g each of the untreated and treated lacquers were applied to a test sheet with a spraying machine and the Sata LP-90 spray gun according to the following settings:
Setting: Needle: 1.3.4
   Pressure: 4 bar
Runs: The number of spray runs was chosen such that there was a dry lacquer layer thickness of 15-20 µm.

Conventionally, effect pigments are regarded as being shear-stable when the gloss differential and the color differential, measured close to the specular angle, is relatively low in the application after the Waring blender test. The $\Delta C^*$ 15° value relative to the untreated sample should ideally be less than 2. Table 6 shows the change in color $\Delta C^*$ 15° and the change in gloss $\Delta 60°$ gloss of the sample that has been subjected to the Waring blender test relative to the untreated sample for inventive examples 5 and 10.

TABLE 6

Gloss differential and color differential in the Waring blender test

| | $\Delta C^*$ (15°) | $\Delta$gloss (60°) |
|---|---|---|
| Example 5 | 0.9 | −1.3 |
| Example 10 | 1.3 | −0.8 |

The absorbent effect pigments of the invention from examples 5 and 10 fulfill the criteria of the test. The color difference is negligibly small. Even under the microscope, it was barely possible to detect any changes such as flaking of the coating or other surface defects that have arisen.

The absorbent effect pigments of the invention are found to be extremely shear-stable in spite of their spacer layer.

IIg Determination of Chemical Stability

The chemical stability of the absorbent effect pigments of the invention and of the pigments from the comparative examples was determined with reference to applications of lacquer to plastic panels. 6 g of the respective pigment were stirred into a mixture of 90 g of a conventional colorless acrylic lacquer and 10 g of butyl acetate 85. Thereafter, the viscosity was adjusted with a mixture of butyl acetate 85 and xylene in a ratio of 1:1 to 17" in the DIN 4 mm cup.

100 g of this lacquer in each case were applied to the panels in hiding application analogously to IIf with a spraying machine. After the coating, the panels were baked at 80° C. for 30 minutes. 24 hours later, the panels were immersed to half their height into 10% sodium hydroxide solution. After a contact time of 7 days, the panels were rinsed with demineralized water and then, after drying time of 2 hours, assessed visually for damage and/or discoloration. In addition, discoloration was analyzed with the aid of the BYK-mac (from Byk-Gardner). The change in color was characterized using the $\Delta E$ value of the exposed sample versus the corresponding unexposed sample at a measurement angle of 15°. The results are shown in table 7 below.

TABLE 7

Color change $\Delta E$

| Example/comparative example | $\Delta E(15°)$ |
|---|---|
| Example 10 | 2.40 |
| Comparative example 3 | 13.31 |

Pigments with $\Delta E(15°)<3$ can be regarded as stable to chemicals. The absorbent effect pigments of the invention from example 10 are below the limit, while the pigments from comparative example 3 distinctly exceed it.

IIh X-Ray Fluorescence Analysis (XRF)

The metal oxide, metal hydroxide and/or metal oxide hydrate contents of the absorbent effect pigments of the invention and of the pigments from the comparative examples were determined by means of x-ray fluorescence analysis (XRF). For this purpose, the respective pigments were incorporated into a lithium tetraborate glass tablet, fixed in solid sample measuring cups and analyzed therefrom. The measuring instrument used was the Advantix ARL system from Thermo Scientific. The measurements are shown in table 8. The figures for the different contents are reported here as $TiO_2$ for titanium, as $Fe_2O_3$ for iron, and as $SnO_2$ for tin.

TABLE 8

Mean height $h_a$ of the spacer layer and XRF values

| Example/ | SEM | XRF (as oxide) | | |
|---|---|---|---|---|
| comparative example | Mean height $h_a$ [nm] | Ti[%] | Fe[%] | Sn[%] |
| Example 1 | 30 | 57.7 | 6.9 | 0.78 |
| Example 2 | 28 | 57.7 | 6.9 | 0.78 |
| Example 3 | 20 | 47.2 | 5.8 | 0.55 |
| Example 4 | 25 | 28.6 | 3.1 | 0.98 |
| Example 5 | 38 | 54.9 | 10.6 | / |
| Example 6 | 55 | / | 65.8 | 4.3 |
| Example 7 | 51 | 48.2 | 0.04 | 3.1 |
| Example 8 | / | / | / | / |
| Example 10 | 20 | 9.1 | 51.1 | / |
| Example 12 | 20 | 23.9 | 4.6 | 1.26 |
| Comparative example 1 | no spacer layer | / | / | / |
| Comparative example 2 | no spacer layer | / | / | / |
| Comparative example 3 | no spacer layer | / | / | / |

III CONDENSATE WATER TEST

To determine condensate water stability, the absorbent effect pigments of the invention and the pigments from the comparative examples were incorporated into a waterborne lacquer system and the test applications were produced by spray painting onto aluminum sheets. The basecoat was overcoated with a conventional one-component clearcoat and then baked. These applications were tested according to DIN 50 017 (water condensation-constant atmospheres). Bond strength was tested by means of cross-cutting according to DIN EN ISO 2409 immediately after the end of the test by comparison with the unexposed sample. In this context, Cc 0 means no change and Cc 5 a very significant change.

The swelling characteristics were visually assessed immediately after condensate water exposure in accordance with DIN 53230. In this context, the index 0 means no change and the index 5 a very significant change.

Finally, the DOI (distinctness of image) was determined with the aid of a Wave-scan II from Byk-Gardner.

TABLE 9

Condensate water results

| Sample | 20° gloss before CW test | 20° gloss after CW test | Loss of gloss | DOI | Cross-cutting immediate | Swelling visual |
|---|---|---|---|---|---|---|
| Example 9 | 90.3 | 89.7 | <1% | 78.2 | 0 | 0 |
| Example 11 | 92.8 | 90.6 | 2.4% | 80.1 | 1 | 0 |
| Comparative example 2 | 91.2 | 21.7 | 76% | n.d. | 5 | 4 |

The pigment from comparative example 2 had significant swelling characteristics and poor interlayer adhesion. The DOI was no longer measurable because of the high degree of fine structure after condensate water exposure.

The absorbent effect pigments of the invention from examples 9 and 11, by contrast, were found to be stable and exhibited virtually no changes before and after the test.

IIj UV Stability

The UV stability of the absorbent effect pigments of the invention and of the pigments from the comparative examples was determined in accordance with the quick UV test described in EP 0 870 730 A1 for determination of the photochemical UV activity of $TiO_2$ pigments. For this purpose, 1.0 g of the corresponding pigment were dispersed into 9.0 g of a double bond-rich melamine-containing lacquer. Applicator drawdowns on white cardboard were produced and dried at room temperature. The applicator drawdowns were divided and one of the two sections of each was stored in the dark as an unexposed comparative specimen. Subsequently, the samples were irradiated with UV-containing light (UVA-340 lamp, irradiation intensity 1.0 W/m$^2$/nm) in a QUV system from Q-Panel for 150 minutes. Immediately after the end of the test, a Minolta CM-508i colorimeter was used to determine color values for the exposed samples relative to the respective reference sample. The resulting $\Delta E^*$ values, calculated according to the Hunter L*a*b* formula, are shown in table 9.

In this test, essentially a gray/blue color of the $TiO_2$ layer of the respective pigment is observed owing to Ti(III) species formed under UV light. A condition for this is that the electron hole has left the environment of the $TiO_2$ and cannot recombine directly with the remaining electron again—for instance through reaction with olefinic double bonds of the binder. Since a melamine-containing lacquer layer significantly slows the diffusion of water (vapor) and oxygen to the pigment surface, reoxidation of the titanium (III) species takes place at a significantly retarded rate, and so the graying can be measured and the $\Delta E^*$ value can be used as a measure for the UV stability of the pigments. A relatively large numerical $\Delta E^*$ value of the exposed sample relative to the unexposed reference sample thus means relatively low UV stability of the pigment examined.

TABLE 10

UV test results

| Example/ comparative example | $\Delta E^*$ |
|---|---|
| Example 5 | 3.23 |
| Example 10 | 2.96 |
| Comparative example 1 | 7.28 |

The comparative example had a much greater change in color ($\Delta E^*$) after corresponding exposure.

IIk Determination of the Mean Thickness of the Nonmetallic Substrates in Platelet Form, the Mean Layer Thickness of Layers 2 and 3, the Mean Layer Thickness of the Overall Coating, the Mean Height $h_a$ of the Spacer Layer and the Mean Height $h_H$ of the Cavities For this purpose, the absorbent effect pigments of the invention were incorporated in a concentration of 10% into a two-component clearcoat, Autoclear Plus HS from Sikkens GmbH, with a sleeved brush, applied to a film with the aid of a spiral applicator (wet film thickness 26 μm) and dried. After a drying time of 24 h, transverse sections of these applicator drawdowns were produced. The transverse sections were analyzed by SEM, with analysis of at least 100 individual pigments to be statistically meaningful for determination of the mean thickness of the nonmetallic substrates in platelet form. To determine the mean layer thickness of layers 2 and 3, the mean thickness of the overall coating, the mean height $h_a$ of the spacer layer and the mean height $h_H$ of the cavities, the upper and lower substrate surfaces, i.e.

the longer side of the nonmetallic substrate in platelet form recognizable in each case in the SEM transverse section, were each used as the baseline. The baseline was drawn here along the surface of the substrate in platelet form in the scanning electron micrograph of the transverse section by connecting the two points of intersection of nonmetallic substrate in platelet form—optional layer 1 or of nonmetallic substrate in platelet form—layer 2 from the left- and right-hand edges of the scanning electron micrograph of the transverse section to one another by means of a straight line. The scanning electron micrographs of transverse images were analyzed with the aid of the AxioVision 4.6.3 image processing software (from Zeiss).

A sufficient number of parallel lines were drawn at 50 nm intervals at a 90° angle from these two baselines as to place a grid over the complete scanning electron micrograph of the transverse section of the effect pigment (FIG. 4). The magnification of the scanning electron micrograph of the transverse section was preferably at least 50 000-fold, based on Polaroid 545. Proceeding from the respective upper and lower baselines of the nonmetallic substrate in platelet form in the direction of layer 3 in each case, the distances between the points of intersection of these lines at the respective interfaces of the optional layer 1 with layer 2, of layer 2 with the spacer layer, of spacer layer with layer 3 and of layer 3 with the environment were measured manually. It happened here that a line marked at 50 nm intervals was located directly above a connection point or a spacer. In this case, only the respective point of intersection at the interface of line 3 with the environment was recorded. These measurements yielded the layer thicknesses of layers 2 and 3, the thickness of the overall coating, and the height $h_a$ of the spacer layer by formation of differences.

For the determination of the mean height $h_H$ of the cavities, the points of intersection of these parallel lines with the upper and lower cavity boundaries within the spacer layer were used.

The individual values of the layer thicknesses, the height $h_a$ and the height $h_H$ that have been determined in this way were used to form the respective arithmetic means in order to determine the above-specified values for the mean layer thicknesses, the mean height $h_H$ and the mean height $h_a$. To be statistically meaningful, the above-described measurements were conducted on at least 100 lines. The term "mean" in all cases means the arithmetic mean.

Transverse sections of the pigments from the comparative examples that do not have a spacer layer but may have statistically distributed pores within the coating were likewise examined by the method described above using scanning electron micrographs of transverse sections. In this case, if one of the parallel lines occurred above one or more pores, the height of the pore(s), the pore midpoint(s) thereof and the distance of the pore midpoint(s) from the substrate surface were determined.

As an alternative to transverse sections, the absorbent effect pigments of the invention can be cut by means of the FIB method (FIB=focused ion beam). For this purpose, a fine beam of highly accelerated ions (for example gallium, xenon, neon or helium) is focused to a point by means of ion optics and guided line by line over the effect pigment surface to be processed. On impact with the effect pigment surface, the ions release most of their energy and destroy the coating at this point, which leads to removal of material line by line. It is also possible using the scanning electron micrographs that have then been recorded, by the method described above, to determine the mean height $h_a$, the mean layer thickness of layers 2 and 3 and the mean layer thickness of the overall coating. The mean thickness of the nonmetallic substrate in platelet form can also be determined using scanning electron micrographs of the effect pigments that have been cut by the FIB method.

The advantages of the absorbent effect pigments of the invention are therefore apparent in the sum total of various properties. The absorbent effect pigments of the invention have high transparency, very good mechanical and chemical stability, and high gloss and color intensity. None of the comparative pigments considered overall has all the properties mentioned in a satisfactory manner.

TABLE 11

Characterization of the coating

| Example/comparative example | $d_{S2}$ [nm] | $d_{S3}$ [nm] | $d_{S2}/d_{S3}$ | $h_{ma}$ [nm] | $h_{Rma}$ | $\sigma h_{Rma}$ [%] | $n_S$ | $S_D$ [%] | $A_H$ [%] |
|---|---|---|---|---|---|---|---|---|---|
| Example 1 | 85 | 91 | 0.94 | 100.4 | 0.49 | 3.8 | 1.1 | 5.4 | 94.6 |
| Example 3 | 66 | 65 | 1.02 | 76.3 | 0.50 | 5.1 | 4.6 | 16.4 | 83.6 |
| Example 5 | 83 | 105 | 0.79 | 94.7 | 0.52 | 4.9 | 3.2 | 15.9 | 84.1 |
| Example 6 | 70 | 99 | 0.71 | 87.6 | 0.44 | 6.5 | 2.2 | 11.0 | 89.0 |
| Example 7 | 55 | 57 | 0.96 | 62.0 | 0.49 | 13.5 | 3.6 | 18.1 | 81.9 |
| Example 10 | 118 | 82 | 1.43 | 128.3 | 0.58 | 4.5 | 6.2 | 30.9 | 69.1 |
| Example 12 | 100 | 118 | 0.85 | 110 | 0.46 | 4.9 | 2.2 | 11.1 | 88.9 |
| Comparative example 1 | | | no spacer layer | | | 21.3 | 18 | 90.0 | 10.0 |
| Comparative example 2 | | | no spacer layer | | | 24.7 | 13 | 65.0 | 35.0 |

$d_{S2}$ [nm] = mean layer thickness of layer 2
$d_{S3}$ [nm] = mean layer thickness of layer 3
$n_S$ = mean number of bars per μm
$A_H$ [%] = area proportion of cavities
$S_D$ = network density [%]
$h_{ma}$ = midpoint of the spacer layer (sum total of the layer thickness of the optional layer 1 and of layer 2 and half the height $h_a$)
$h_{Rma}$ = relative height of the spacer layer
$\sigma h_{Rma}$ [%] = standard deviation of the relative height of the spacer layer Table 8 shows the mean height $h_a$ of the spacer layer of the pigments examined. All the absorbent effect pigments of the invention, by contrast with the pigments from comparative examples 1 to 3, have a spacer layer.

The pigments from comparative examples 1 and 2 do not have a spacer layer, but have a statistical distribution of pores within the coating. In table 11, for comparative examples 1 and 2, the value in the $\sigma h_{Rma}$ [%] column means the standard deviation of the pore midpoints from the substrate surface. Since the pigment from comparative example 2, however, contains only few statistically distributed pores, the network density SD is 65.0%. The standard deviation of the pore midpoints from the substrate surface is 24.7%, which demonstrates that the pores are statistically distributed within the overall coating. The situation is different for the absorbent effect pigments of the invention from examples 1, 3, 5 to 7 and 10. Here, the standard deviation of the relative height of the midpoint of the spacer layer $h_{Rma}$ is <14% in each case, which indicates that the respective spacer layer thereof is at a defined position within the coating. The standard deviation of the distances of the pore midpoints from the substrate surface of the pigment from comparative examples 1 and 2 can thus be compared with the standard deviation of the relative height of the midpoint of the spacer layer of the absorbent effect pigments of the invention.

III Scanning Electron Micrographs

The scanning electron micrographs were obtained using transverse sections of the absorbent effect pigments of the invention with the Supra 35 scanning electron microscope (from Zeiss). Energy-dispersive x-ray micro-analysis (EDX analysis) was conducted with the EDAX Sapphire instrument, from EDAX.

III APPLICATION EXAMPLES

Application Example 1: Body Lotion

| INCI name | Product name | % by wt. | Manufacturer/ supplier |
|---|---|---|---|
| Phase A | | 85.80 | |
| | Effect pigment from example 1 | 0.20 | |

-continued

| INCI name | Product name | % by wt. | Manufacturer/ supplier |
|---|---|---|---|
| Aqua | Water | | |
| Glycerin | Glycerin 85% | 2.00 | H. Erhard Wagner |
| Xanthan Gum | Keltrol CG-T | 0.60 | CP Kelco |
| Phase B | | | |
| Isopropyl Palmitate | Isopropyl palmitate | 3.00 | H. Erhard Wagner |
| Glyceryl Stearate | Aldo MS K FG | 2.00 | Lonza |
| *Cocos Nuifera* Oil | Ewanol KR | 2.00 | H. Erhard Wagner |
| Cetearyl Alcohol | Tego Alkanol 1618 | 2.00 | Evonik |
| Dimethicone | Element 14 PDMS | 1.00 | Momentive |
| Sodium Polyacrylate | Cosmedia SP | 0.50 | BASF |
| Phase C | | | |
| Phenoxyethanol, Ethylhexylglycerin | Euxyl PE 9010 | 0.80 | Schülke & Meyr |
| Fragrance | Vitamin Bomb | 0.10 | Bell Europe |

The effect pigment from example 1 can be used within a range from 0.1% to 2.5% by weight, based on the total weight of the body lotion formulation. Compensation to 100% by weight of the formulation can be effected with water.

Keltrol CG-T was dispersed in phase A and heated to 75° C. Phase B was heated separately to 75° C. Subsequently, phase B was added gradually to phase A. The emulsion was cooled down to room temperature while stirring and phase C was added individually.

Application Example 2: Eyeshadow Cream

| INCI name | Product name | % by wt. | Manufacturer/ supplier |
|---|---|---|---|
| Phase A | | | |
| Microcrystalline Wax | TeCero-Wax 1030 K | 4.50 | Tromm Wachs |
| *Copernicia Cerifera* Cera | LT 124 carnauba wax | 4.50 | Tromm Wachs |
| Isohexadecane | Isohexadecane | 21.00 | Ineos |
| Cyclopentasiloxane, Dimethicone/Vinyltrimethylsiloxysilicate Crosspolymer | Belsil RG 100 Silicone Elastomer Resin Gel | 8.00 | Wacker |
| Trimethylsiloxyphenyl Dimethicone | Belsil PDM 20 | 6.00 | Wacker |
| Dimethicone | Belsil DM 100 | 14.00 | Wacker |
| Caprylic/Capric Triglyceride | Miglyol 812 | 7.00 | Sasol |
| Cyclomethicone (and) Quaternium-90 Bentonite (and) Propylene Carbonate | Tixogel VSP-1438 | 5.00 | BYK |
| Phase B | | | |
| | Effect pigment from example 3 | 30.00 | |

The effect pigment from example 3 can be used within a range from 5% to 30.0% by weight, based on the total weight of the eyeshadow formulation. Compensation to 100% by weight of the formulation can be effected with isohexadecane.

Phase A was mixed and heated to 85° C., then phase B was added to phase A while stirring. After dispensing into an appropriate container, the mixture is cooled to room temperature.

Application Example 3: Shower Gel

| INCI name | Product name | % by wt. | Manufacturer/supplier |
|---|---|---|---|
| Phase A | | | |
| | Effect pigment from example 5 | 0.10 | |
| Aqua | Water | 58.50 | |
| Acrylates Copolymer | Carbopol Aqua SF-1 | 5.50 | Lubrizol |
| Phase B | | | |
| Sodium Hydroxide | NaOH (10% by wt.) | 1.50 | |
| Phase C | | | |
| Sodium Laureth Sulfate | Zetesol NL-2 U | 22.00 | Zschimmer & Schwarz |
| Cocamidopropyl Betaine | Amphotensid B5 | 6.00 | Zschimmer & Schwarz |
| PEG-7 Glyceryl Cocoate | Emanon HE | 2.00 | Kao Corp. |
| Disodium Laureth Sulfosuccinate | Sectacin 103 Spezial | 2.00 | Zschimmmer & Schwarz |
| Phase D | | | |
| Phenoxyethanol (and) Piroctone Olamine | Nipaguard PO 5 | 0.60 | Clariant |
| Fragrance | Water Lily OA | 0.20 | Bell Flavors and Fragrances |
| Sodium Chloride | Sodium Chloride | 1.60 | VWR |

The effect pigment from example 5 can be used within a range from 0.01% to 1.0% by weight, based on the total weight of the shower gel formulation. Compensation to 100% by weight of the formulation can be effected with water.

Phase A was stirred, then phase B was added and stirred until a homogeneous appearance was achieved. Phase C was weighed out separately, mixed briefly and added to phase AB. Subsequently, the mixture was stirred again and phase D was added individually.

Application Example 4: Eyeshadow Compact

| INCI name | Product name | % by wt. | Manufacturer/supplier |
|---|---|---|---|
| Phase A | | | |
| Talc | Talc Powder | 36.00 | VWR |
| Bentonite | Optigel CK-PC | 5.00 | BYK |
| Synthetic Fluorphlogopite | Synafil S 1050 | 13.00 | ECKART |

-continued

| INCI name | Product name | % by wt. | Manufacturer/supplier |
|---|---|---|---|
| Aluminium Starch Octenylsuccinate | Agenaflo OS 9051 | 10.00 | Agrana |
| Magnesium Stearate | Magnesium Stearate | 6.00 | VWR |
| | Effect pigment from example 8 | 20.00 | |
| Phase B | | | |
| Cyclomethicone | Xiameter PMX-0345 | 5.00 | Dow Corning |
| Octyldodecyl Stearoyl Stearate | Ceraphyl 847 | 5.00 | Ashland |

The effect pigment from example 8 can be used within a range from 5.0% to 40.0% by weight, based on the total weight of the eyeshadow formulation. Compensation to 100% by weight of the formulation can be effected with talc.

Phase A was mixed in a high-speed mixer at 2500 rpm for 30 s. Subsequently, phase B was added and the mixture was mixed in the same mixer at 3000 rpm for 60 s. Finally, the powder mixture was pressed into shape by means of an eyeshadow press at 100 bar for 30 seconds.

Application Example 5: Mascara

| INCI name | Product name | % by wt. | Manufacturer/supplier |
|---|---|---|---|
| Phase A | | | |
| Aqua | Water | 73.00 | |
| Bentonite (and) Xanthan Gum | Optigel WX-PC | 2.00 | BYK |
| Phase B | | | |
| Cetyl Alcohol (and) Glyceryl Stearate (and) PEG-75 Stearate (and) Ceteth-20 (and) Steareth-20 | Emulium Delta | 5.00 | Gattefosse |
| C10-18 Triglycerides | Lipocire A Pellets | 2.00 | Gattefosse |
| Ozokerite | Kahlwax 1899 | 2.00 | Kahl |

| INCI name | Product name | % by wt. | Manufacturer/supplier |
|---|---|---|---|
| Glyceryl Behenate | Compritol 888 CG Pastilles | 2.00 | Gattefosse |
| Butylene Glycol Cocoate | Cocoate BG | 4.00 | Gattefosse |
| Phase C | | | |
| | Effect pigment from example 8 | 5.00 | |
| Phenoxyethanol (and) Piroctone Olamine | Nipaguard PO5 | 0.50 | Clariant |
| *Glycine Soja* (Soybean) Oil, Dicaprylyl Ether, *Magnolia Grandiflora* Bark Extract, Lauryl Alcohol | Follicusan DP | 3.00 | CLR Berlin |
| Water, Hydrolyzed Corn Starch, *Beta Vulgaris* (Beet) Root Extract | DayMoist CLR | 1.00 | CLR Berlin |
| Linoleic Acid (and) Linolenic Acid | Vitamin F forte | 0.50 | CLR Berlin |

The effect pigment from example 8 can be used within a range from 1.0% to 10.0% by weight, based on the total weight of the mascara formulation. Compensation to 100% by weight of the formulation can be effected with the water from phase A.

Phase A was stirred under high shear. Phase B was weighed out separately. Phase A and phase B were heated separately to 85° C., then phase B was added to phase A. Subsequently, phase AB was cooled to 45° C. and, during the cooling, phase C was added gradually while stirring.

Application Example 6: Hair Gel

| INCI name | Product name | % by wt. | Manufacturer/supplier |
|---|---|---|---|
| Phase A | | | |
| Sodium Magnesium Silicate (nano) | Laponite XLG | 2.00 | BYK |
| Aqua | Water | 94.80 | |
| Phase B | | | |
| | Effect pigment from example 6 | 0.10 | |
| Citric Acid (and) Water | Citric Acid (1 0%) | 0.30 | |
| Glycerin, Water, *Avena Strigosa* Seed Extract, Lecithin, Potassium Sorbate, Citric Acid | Aquarich | 1.50 | Rahn AG |
| Fragrance | Lychee & Grape | 0.10 | Bell Europe |
| Methylisothiazolinone (and) Phenethyl Alcohol (and) PPG-2-Methyl Ether | Optiphen MIT Plus | 1.20 | Ashland |

The effect pigment from example 6 can be used within a range from 0.01% to 2.0% by weight, based on the total weight of the hair gel formulation. Compensation to 100% by weight of the formulation can be effected with water.

The Laponite XLG was stirred with water until phase A became clear. Then the effect pigment from example 6 was added to phase B while stirring. Subsequently, the rest of the ingredients of phase B were added gradually.

Application Example 7: Body Powder

| INCI name Phase A | Product name | % by wt. | Manufacturer/supplier |
|---|---|---|---|
| Synthetic Fluorphlogopite | Synafil S 1050 | 40.00 | Eckart |
| Polypropylene | Synafil W 1234 | 8.00 | Eckart |
| Bentonite | Optigel CK-PC | 10.00 | BYK |
| Talc | Talc Powder | 18.00 | VWR |
| Magnesium Stearate | Magnesium Stearate | 4.00 | Applichem |
| | Effect pigment from example 5 | 20.00 | |

The effect pigment from example 5 can be used within a range from 0.2% to 5.0% by weight, based on the total weight of the body powder formulation. Compensation to 100% by weight of the formulation can be effected with Synafil S 1050.

Phase A was mixed and then the powder was dispensed into a suitable vessel.

Application Example 8: Lipgloss

| INCI name Phase A | Product name | % by wt. | Manufacturer/supplier |
|---|---|---|---|
| Hydrogenated Polyisobutene (and) Ethylene/Propylene/Styrene Copolymer (and) Butylene/Ethylene/Styrene Copolymer | Versagel ME 750 | 75.30 | Penreco |

| INCI name | Product name | % by wt. | Manufacturer/supplier |
|---|---|---|---|
| *Simmondsia Chinensis* (Jojoba) Seed Oil | Jojoba Oil - Natural | 2.00 | BioChemica |
| Caprylyl Trimethicone | Silcare Silicone 31M50 | 7.00 | Clariant |
| Stearyl Dimethicone | Silcare Silicone 41M65 | 3.20 | Clariant |
| Hydrogenated Polydecene | Dekanex 2004 FG | 4.00 | IMCD |
| Isopropyl Myristate | Isopropyl Myristate | 4.50 | VWR |

| INCI name | Product name | % by wt. | Manufacturer/supplier |
|---|---|---|---|
| Phase B | | | |
| | Effect pigment from example 6 | 4.00 | |

The effect pigment from example 6 can be used within a range from 0.10% to 8.00% by weight, based on the total weight of the lipgloss formulation. Compensation to 100% by weight of the formulation can be effected with Versagel ME 750.

Phase A was heated to 85° C., then the pigment from example 6 was added to phase B and stirred until the consistency was homogeneous, and then dispensed into a lipgloss vessel.

Application Example 9: Lipstick

| INCI name | Product name | % by wt. | Manufacturer/supplier |
|---|---|---|---|
| Phase A | | | |
| Octyldodecanol | Eutanol G | 42.5 | BASF |
| Candelilla Cera | Kahlwax 2039 | 6.00 | Kahl |
| *Copernicia Cerifera* (Carnauba) Wax | Kahlwax 2442 | 6.00 | Kahl |
| Bis-Diglyceryl Polyacyladipate-2 | Softisan 649 | 10.00 | Sasol |
| Polyisobutene | Rewopal PIB 1000 | 10.00 | Evonik |
| Hydrogenated Polydecene | Silkflo 364 NF Polydecene | 5.00 | Ineos |
| C10-18 Triglycerides | Lipocire A Pellets | 5.00 | Gattefosse |
| *Acacia Decurrens*/Jojoba/Sunflower Seed Wax/Polyglyceryl-3 Esters | Hydracire S | 5.00 | Gattefosse |
| Tocopheryl Acetate | dl-alpha-Tocopheryl | 0.50 | IMCD |
| Phase B | | | |
| | Effect pigment from example 10 | 10.00 | |

The effect pigment from example 10 can be used within a range from 0.5% to 20.0% by weight, based on the total weight of the lipstick formulation. Compensation to 100% by weight of the formulation can be effected with Eutanol G.

Phase A was heated to 85° C., then phase B was added to phase A and mixed. Subsequently, this mixture was dispensed into a lipstick mold at a temperature of 75° C.

Application Example 10: Liquid Eyelid Liner

| INCI name | Product name | % by wt. | Manufacturer/supplier |
|---|---|---|---|
| Phase A | | | |
| Aqua | Water | 56.90 | |
| Bentonite (and) Xanthan Gum | Optigel WX-PC | 1.40 | |
| Phase B | | | |
| Lecithin | Emulmetik 100 | 0.10 | Lucas Meyer |
| *Copernicia Cerifera* Cera | Kahlwax 2442 | 1.00 | Kahl |
| Stearic Acid | Stearic Acid | 3.50 | Lipo Chemicals |
| Hydrogenated Polyisobutene | Panalane L14 E | 5.00 | Ineos |
| Polysorbate 60 | Mulsifan CPS 60 | 1.50 | Zschimmer & Schwarz |

-continued

| INCI name | Product name | % by wt. | Manufacturer/supplier |
|---|---|---|---|
| Phase C | | | |
| | Effect pigment from example 2 | 4.00 | |
| Polyurethane-35 | Baycusan C 1004 | 18.00 | Bayer Cosmetics |
| Aqua and CI 77499 and Methylpropanediol and Ammonium Acrylates Copolymer and Simethicone and Caprylyl Glycol and Phenylpropanol Sodium Acrylates Copolymer | WorléeBase AQ 77499/1 | 8.00 | Worlée |
| Phenoxyethanol, Ethylhexylglycerin | Euxyl PE 9010 | 0.60 | Schülke & Mayr |

The effect pigment from example 2 can be used within a range from 0.5% to 8.0% by weight, based on the total weight of the eyelid liner formulation. Compensation to 100% by weight of the formulation can be effected with water.

Optigel WX-PC was dispersed in water of phase A and stirred for 10 minutes. Phase A and phase B were heated separately to 80° C. Thereafter, phase B was added gradually to phase A while stirring. After cooling to 45° C., the ingredients of phase C were added gradually and the mixture was dispensed into a suitable package.

Application Example 11: Mousse

| INCI name | Product name | % by wt. | Manufacturer/supplier |
|---|---|---|---|
| Phase A | | | |
| Cyclopentasiloxane | Xiameter PMX-0245 Cyclosiloxane | 8.60 | Dow Corning |
| Hydrogenated Polyisobutene | MC 30 | 4.00 | Sophim |
| Dimethicone (and) Dimethicone Crosspolymer | Dow Corning 9041 Silicone Elastomer Blend | 37.14 | Dow Corning |
| Squalane | Squalane | 5.74 | Impag |
| Isononyl Isononanoate | Dermol 99 | 10.16 | Akzo International |
| Hydrogenated Jojoba Oil | Jojoba Butter LM | 2.15 | Desert Whale |
| Hydrogenated Jojaba Oi | Jojoba Butter HM | 1.00 | Desert Whale |
| C30-45 Alkyl Methicone (and) C30-45 Olefin | Dow Corning AMS-C30 Cosmetic Wax | 1.15 | Dow Corning |
| Stearyl Dimethicone | Dow Corning 2503 Cosmetic Wax | 0.47 | Dow Corning |
| Cyclopentasiloxane (and) Polypropylsilsesquioxane | Dow Corning 670 Fluid | 5.00 | Dow Corning |
| Phase B | | | |
| Dimethicone/Vinyl Dimethicone Crosspolymer | Dow Corning 9506 Powder | 16.02 | Dow Corning |
| Silica Dimethyl Silylate | Covasilic 15 | 0.17 | LCW |
| Talc | Talc Powder | 5.00 | Sigma-Aldrich |
| | Effect pigment from example 4 | 3.00 | |
| Phase D | | | |
| Phenoxyethanol, Ethylhexylglycerin | Euxyl PE 9010 | 0.40 | Schülke & Mayr |

The effect pigment from example 4 can be used within a range from 0.1% to 8.0% by weight, based on the total weight of the mousse formulation. Compensation to 100% by weight of the formulation can be effected with Dow Corning 9041 Elastomer.

Phase A was mixed and heated until everything had melted. Phase B was weighed out separately and mixed with a high-speed mixer at 2400 rpm for 60 s. Half of the molten phase A was added to phase B and the mixture was mixed again in the mixer at 2400 rpm for 30 s. Subsequently, the remaining portion of phase B was likewise added to phase A and the mixture was mixed again at 2400 rpm for 30 s. Lastly, phase C was added to phase AB and the mixture was mixed again in the high-speed mixer at 2400 rpm for 30 s.

Application Example 12: Nail Varnish

| INCI name | Product name | % by wt. | Manufacturer/supplier |
|---|---|---|---|
| Phase A | | | |
| | Effect pigment from example 6 | 4.00 | |
| Phase B | | | |
| Butylacetat (and) Ethylacetat (and) Nitrocellulose (and) Isopropyl Alcohol | International Lacquers Nailpolish Base 15244 | 96.00 | International Lacquers |

The effect pigment from example 6 can be used within a range from 0.1% to 8.0% by weight, based on the total weight of the nail varnish formulation. Compensation to 100% by weight of the formulation can be effected with International Lacquers Nailpolish.

Phase A and phase B were mixed and then dispensed into an appropriate container.

Application Example 13: Nail Varnish with Soft-Touch Effect

| INCI name | Product name | % by wt. | Manufacturer/supplier |
|---|---|---|---|
| Phase A | | | |
| | Effect pigment from example 10 | 4.00 | |
| Polypropylene | Synafil W 1234 | 5.00 | Eckart |
| Phase B | | | |
| Butylacetat (and) Ethylacetat (and) Nitrocellulose (and) Isopropyl Alcohol | International Lacquers Nailpolish Base 15244 | 91.00 | International Lacquers |

The effect pigment from example 10 can be used within a range from 0.1% to 8.0% by weight, based on the total weight of the nail varnish formulation. Compensation to 100% by weight of the formulation can be effected with International Lacquers Nailpolish.

Phase A was mixed and added to phase B, and then the nail varnish was dispensed into an appropriate container.

Application Example 14: Aqueous Nail Varnish

The effect pigments from examples 1 to 8 and from example 10 can be used in an aqueous nail varnish according to WO 2007/115675 A2 example 1. The pigmentation level here is 0.1% to 10.0% by weight, based on the total weight of the formulation.

Application Example 15: Liquid Eyeshadow

| INCI name | Product name | % by wt. | Manufacturer/supplier |
|---|---|---|---|
| Phase A | | | |
| Water | Aqua | 73.80 | |
| Glycerin | Glycerin | 3.00 | H. Erhard Wagner |
| Phase B | | | |
| PEG-800 | Polyglycol 35000 S | 0.60 | Clariant |
| Ammonium Acryloyldimehtyltaurate/VP Copolymer | Aristoflex AVC | 0.80 | Clariant |
| Acrylates Copolymer | Worlee Micromer CEK 20/50 | 5.00 | Worlee |
| Phase C | | | |
| | Effect pigment from example 3 | 10.00 | |
| Divinyldimethicone/Dimethicone Copolymer C12-C13 Pareth-3, C12-C13 Pareth-23 | Dow Corning HMW 2220 Non-Ionic Emulsion | 6.00 | Dow Corning |
| Phenoxyethanol, Ethylhexylglycerin | Euxyl PE9010 | 0.80 | Schülke & Mayr |

The effect pigment from example 3 can be used within a range from 0.10% to 20.00% by weight, based on the total weight of the eyeshadow formulation. Compensation to 100% by weight of the formulation can be effected with water.

Phase A was stirred, then the ingredients of phase B were added individually to phase A and stirred until the consistency was homogeneous. Thereafter, the ingredients of phase C were added individually to phase AB and the mixture was stirred until the consistency was homogeneous.

FIG. 1: Scanning electron micrograph of a transverse section of an effect pigment of the invention in 50 000-fold magnification (based on Polaroid 545).

Figure 2:
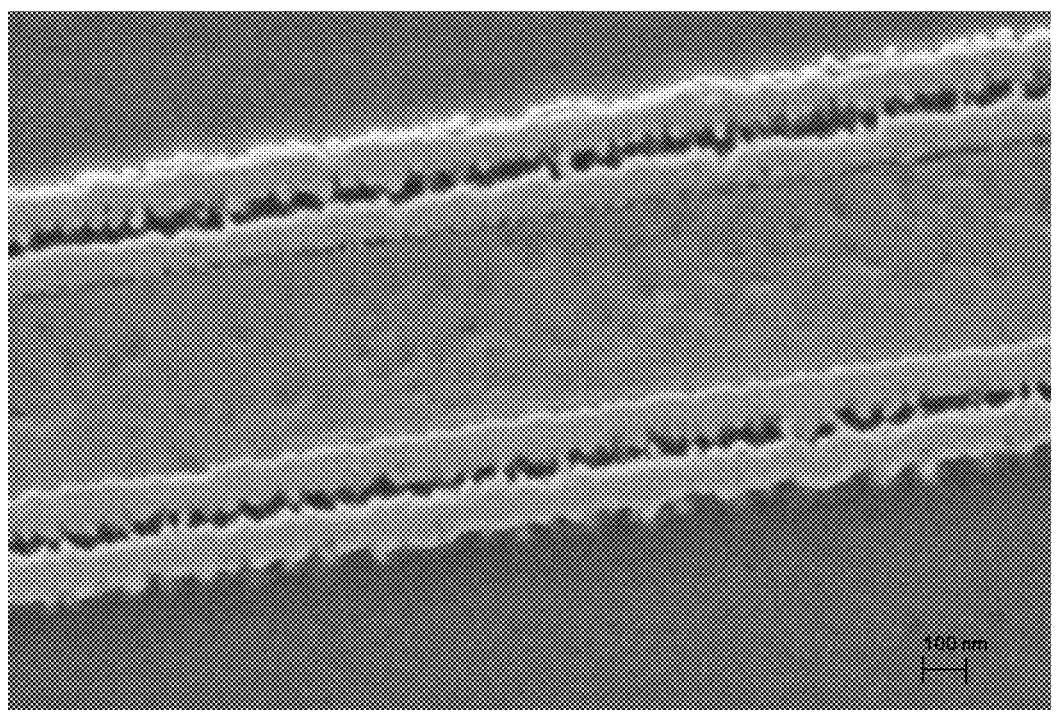
FIG. 2 is a scanning electron micrograph of a transverse section of an effect pigment of the invention in 50,000-fold magnification (based on Polaroid 545)

FIG. 2: Scanning electron micrograph of a transverse section of an effect pigment of the invention in 50 000-fold magnification (based on Polaroid 545).

Figure 3:
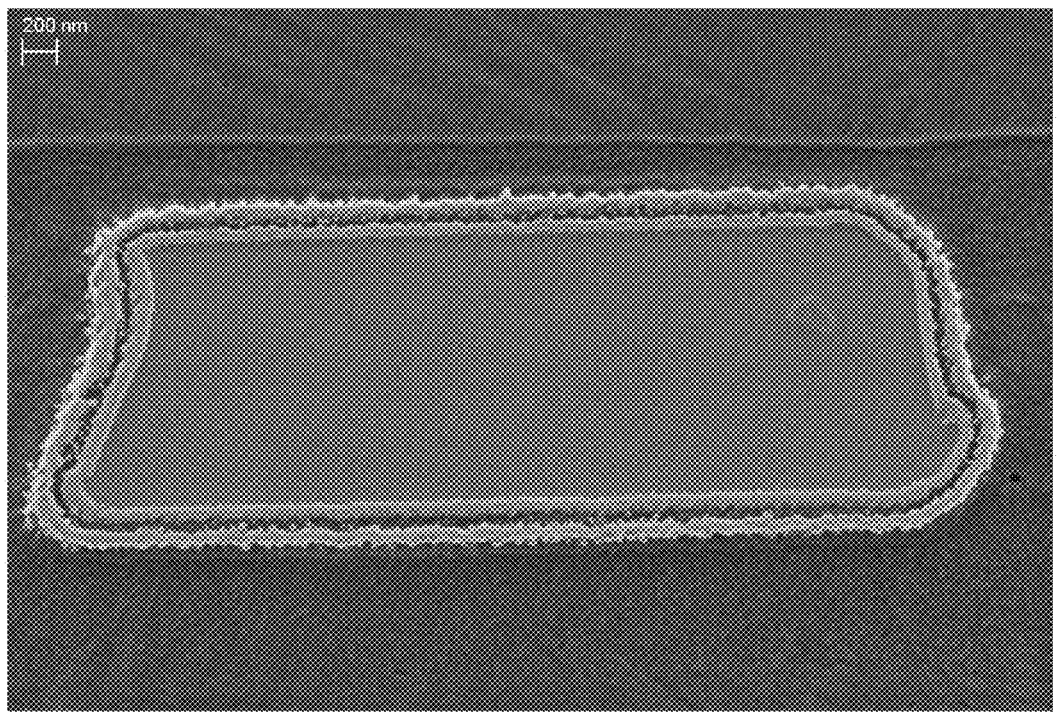
FIG. 3 is a scanning electron micrograph of a transverse section of an effect pigment of the invention in 20,000-fold magnification (based on Polaroid 545)

FIG. 3: Scanning electron micrograph of a transverse section of an effect pigment of the invention in 20 000-fold magnification (based on Polaroid 545).

FIG. 4: Detail of the scanning electron micrograph of a transverse section from FIG. 2 with a baseline drawn in at the interface of nonmetallic substrate in platelet form— coating, and lines arranged at right angles to the baseline. "x" marks the points of intersection at the interfaces.

FIG. 5: Scanning electron micrograph of a transverse section of the titanium dioxide-coated pearlescent pigment SYMIC C261 (from ECKART GmbH) in 20 000-fold magnification (based on Polaroid 545).

FIG. 6: Schematic diagram of the spacer layer.

FIG. 7: Schematic diagram of the position of the spacer layer.

FIG. 8: Concentration profile (line scan) using a transverse section in a scanning electron microscope with energy-dispersive microanalyzer (EDX) of example 12 prior to calcination.

FIG. 9: Concentration profile (line scan) using a transverse section in a scanning electron microscope with energy-dispersive microanalyzer (EDX) of example 12 after calcination.

The invention claimed is:

1. An absorbent effect pigment comprising a nonmetallic substrate in platelet form and a coating applied to the substrate, wherein the coating comprises
a) optionally a layer 1 comprising or consisting of at least one of tin oxide, tin hydroxide or tin oxide hydrate,
b) a layer 2 having a high refractive index n>1.8, the layer 2 comprising at least one of metal oxide, metal hydroxide or metal oxide hydrate, and
c) a layer 3 having a high refractive index n>1.8, the layer 3 comprising at least one of metal oxide, metal hydroxide or metal oxide hydrate,
at least one of layers 2 and 3 comprises at least two different metal ions and layers 2 and 3 are interrupted by a spacer layer, wherein the at least one spacer layer comprises connections and cavities.

2. The absorbent effect pigment as claimed in claim 1, wherein the nonmetallic substrate in platelet form is selected from the group consisting of natural mica platelets, synthetic mica platelets, iron mica, glass platelets, $SiO_2$ platelets, $Al_2O_3$ platelets, kaolin platelets, talc platelets, bismuth oxychloride platelets and mixtures thereof, and the nonmetallic substrate in platelet form has optionally been coated with at least one of metal oxide, metal hydroxide or metal oxide hydrate.

3. The absorbent effect pigment as claimed in claim 1, wherein the effect pigment comprises further layers of high and/or low refractive index and optionally at least one further spacer layer.

4. The absorbent effect pigment as claimed in claim 1, wherein the at least two different metal ions of layers 2 and 3 are selected from the group of metals consisting of Ti, Fe, Sn, Mn, Zr, Ca, Sr, Ba, Ni, Sb, Ag, Zn, Cu, Ce, Cr and Co, and wherein the proportion of noncoloring metal ions selected from the group of the metals consisting of Ti, Sn, Zr, Ca, Sr, Ba and Zn totals ≤40% by weight, and the proportion of coloring metal ions selected from the group of the metals consisting of Fe, Ti, Sn, Mn, Ni, Sb, Ag, Cu, Ce, Cr and Co totals ≥4% by weight, determined by means of XRF in each case, calculated in each case as the elemental metal and based in each case on the total weight of the absorbent effect pigment of the invention.

5. The absorbent effect pigment as claimed in claim 1, wherein a weight ratio, determined by means of XRF and calculated as the elemental metal, of noncoloring metal ions to coloring metal ions in the absorbent effect pigment of the invention is <20.

6. The absorbent effect pigment as claimed in claim 1, wherein the at least one spacer layer is arranged essentially parallel to the surface of the nonmetallic substrate in platelet form.

7. The absorbent effect pigment as claimed in claim 1, wherein the at least one spacer layer has a mean height $h_a$ from a range from 5 nm to 120 nm.

8. The absorbent effect pigment as claimed in claim 1, wherein the at least one spacer layer has a network density of <85%.

9. An absorbent effect pigment comprising a nonmetallic substrate in platelet form and a coating applied to the substrate, wherein the coating comprises
a) optionally a layer 1 comprising or consisting of at least one of tin oxide, tin hydroxide or tin oxide hydrate,
b) a layer 2 having a high refractive index n>1.8, the layer comprising at least one of metal oxide, metal hydroxide or metal oxide hydrate, and
c) a layer 3 having a high refractive index n>1.8, the layer comprising at least one of metal oxide, metal hydroxide or metal oxide hydrate,
at least one of layers 2 and 3 comprises at least two different metal ions and layers 2 and 3 are interrupted by a spacer layer, wherein the at least one spacer layer comprises connections and cavities, and wherein the spacer layer has a standard deviation of the relative height of $\sigma h_{Rma}$ in a range of 0.2 to 18%, wherein the relative height $h_{Rma}$ is defined as the ratio of the height $h_{ma}$ to the layer thickness of the overall coating and $h_{ma}$ refers to the sum total of the layer thickness of optional layer 1, layer 2 and half the height $h_a$ of the spacer layer.

10. The absorbent effect pigment according to claim 9, wherein the mean height of the spacer layer $h_a$ is determined by the following method:
the effect pigments are applied in a lacquer and cross sections are prepared and scanning electron micrographs analyzed thereof comprising the steps:
establishing the upper and lower substrate surfaces as baselines which are the longer side of the nonmetallic substrate in platelet form in each case and drawing the baselines onto the scanning electron micrograph of the transverse section;
analyzing the scanning electron micrographs of the transverse sections with the aid of the AxioVision 4.6.3 image processing software (from Zeiss);
drawing a sufficient number of parallel lines at 50 nm intervals at a 90° angle with respect to the upper and lower baselines corresponding to the two surfaces of the substrate in platelet form establishing a grid over the effect pigment shown in the scanning electron micrograph of a transverse section (FIG. 4) using a magnification of at least 50,000-fold, based on Polaroid 545 (4"×5");
proceeding from the respective baseline of the nonmetallic substrate in platelet form, in the direction of the respective outer layer 3 or the respective outermost layer, the points of intersection between the parallel lines arranged at right angles to the respective baseline with the respective interfaces of the optional layer 1 with layer 2, of layer 2 with the spacer layer, of the spacer layer with layer 3, and of layer 3 with the environment or with any further layer applied are analyzed manually, wherein in the case that one of the lines drawn at 50 nm intervals occurs directly above a connection point or a spacer only the respective point of intersection of the line at the interface of layer 3 with the environment or with any further layer applied is recorded; and determining the layer thicknesses of layers 2 and 3, the layer thickness of the overall coating, the layer thickness of further layers optionally present, and the height $h_a$ of the spacer layer by formation of differences, wherein the layer thickness of layer 2 is calculated from the difference between the respective measured points of intersection at the respective interfaces of layer 2 with the spacer layer and of either optional layer 1 with layer 2 or the baseline with layer 2 if the nonmetallic substrate in platelet form has not been covered with further layers beforehand, and the layer thickness of layer 3 is calculated from the difference between the respective measured points of intersection of layer 3 with the environment or any further layer applied and of the spacer layer with layer 3 and the height $h_a$ of the spacer layer is calculated from the difference between the respective measured point of intersection of spacer layer with layer 3 and layer 2 with the spacer layer, wherein the height $h_a$ is determined by forming the arithmetic mean by conducting this procedure to at least 100 of the parallel lines arranged at right angles to the baselines.

11. The absorbent effect pigment according to claim 9, wherein the relative height of $\sigma h_{Rma}$ in a range of 0.3 to 15%.

12. The absorbent effect pigment according to claim 9, wherein the nonmetallic substrate in platelet form is selected from the group consisting of natural mica platelets, synthetic mica platelets, iron mica, glass platelets, $SiO_2$ platelets, $Al_2O_3$ platelets, kaolin platelets, talc platelets, bismuth oxychloride platelets and mixtures thereof, and the nonmetallic substrate in platelet form has optionally been coated with at least one of metal oxide, metal hydroxide or metal oxide hydrate.

13. The absorbent effect pigment according to claim 9, wherein the effect pigment comprises further layers of high and/or low refractive index and optionally at least one further spacer layer.

14. The absorbent effect pigment according to claim 9, wherein the at least two different metal ions of layers 2 and 3 are selected from the group of metals consisting of Ti, Fe, Sn, Mn, Zr, Ca, Sr, Ba, Ni, Sb, Ag, Zn, Cu, Ce, Cr and Co, and wherein the proportion of noncoloring metal ions selected from the group of the metals consisting of Ti, Sn, Zr, Ca, Sr, Ba and Zn totals ≤40% by weight, and the proportion of coloring metal ions selected from the group of the metals consisting of Fe, Ti, Sn, Mn, Ni, Sb, Ag, Cu, Ce, Cr and Co totals ≥4% by weight, determined by means of XRF in each case, calculated in each case as the elemental metal and based in each case on the total weight of the absorbent effect pigment of the invention.

15. The absorbent effect pigment according to claim 9, wherein a weight ratio, determined by means of XRF and calculated as the elemental metal, of noncoloring metal ions to coloring metal ions in the absorbent effect pigment of the invention is <20.

16. The absorbent effect pigment according to claim 9, wherein the at least one spacer layer is arranged essentially parallel to the surface of the nonmetallic substrate in platelet form.

17. The absorbent effect pigment according to claim 9, wherein the at least one spacer layer has a mean height $h_a$ from a range from 5 nm to 120 nm.

18. An absorbent effect pigment comprising a nonmetallic substrate in platelet form and a coating applied to the substrate, wherein the coating comprises
   a) optionally a layer 1 comprising or consisting of at least one of tin oxide, tin hydroxide or tin oxide hydrate,
   b) a layer 2 having a high-refractive index n>1.8 the layer 2 comprising at least one of metal oxide, metal hydroxide or metal oxide hydrate, and
   c) a layer 3 having a high-refractive index n>1.8, the layer 3 comprising at least one of metal oxide, metal hydroxide or metal oxide hydrate,
   at least one of layers 2 and 3 comprises at least two different metal ions and layers 2 and 3 are interrupted by a spacer layer, wherein the spacer layer comprises connections and cavities and wherein the spacer layer comprises an area proportion of cavities from a range of 51% 99%, measured from scanning electron micrographs of traverse sections.

19. The absorbent effect pigment according to claim 18, wherein the area proportion of cavities is a range of 63% to 96%.

20. The absorbent effect pigment according to claim 18, wherein the nonmetallic substrate in platelet form is selected from the group consisting of natural mica platelets, synthetic mica platelets, iron mica, glass platelets, $SiO_2$ platelets, $Al_2O_3$ platelets, kaolin platelets, talc platelets, bismuth oxychloride platelets and mixtures thereof, and the nonmetallic substrate in platelet form has optionally been coated with at least one of metal oxide, metal hydroxide or metal oxide hydrate.

21. The absorbent effect pigment according to claim 18, wherein the effect pigment comprises further layers of high and/or low refractive index and optionally at least one further spacer layer.

22. The absorbent effect pigment according to claim 18, wherein the at least two different metal ions of layers 2 and 3 are selected from the group of metals consisting of Ti, Fe, Sn, Mn, Zr, Ca, Sr, Ba, Ni, Sb, Ag, Zn, Cu, Ce, Cr and Co, and wherein the proportion of noncoloring metal ions selected from the group of the metals consisting of Ti, Sn, Zr, Ca, Sr, Ba and Zn totals ≤40% by weight, and the proportion of coloring metal ions selected from the group of the metals consisting of Fe, Ti, Sn, Mn, Ni, Sb, Ag, Cu, Ce, Cr and Co totals ≥4% by weight, determined by means of XRF in each case, calculated in each case as the elemental metal and based in each case on the total weight of the absorbent effect pigment of the invention.

23. The absorbent effect pigment according to claim 18, wherein a weight ratio, determined by means of XRF and calculated as the elemental metal, of noncoloring metal ions to coloring metal ions in the absorbent effect pigment of the invention is <20.

24. The absorbent effect pigment according to claim 18, wherein the at least one spacer layer is arranged essentially parallel to the surface of the nonmetallic substrate in platelet form.

25. The absorbent effect pigment according to claim 18, wherein the at least one spacer layer has a mean height $h_a$ from a range from 5 nm to 120 nm.

26. A process for producing the absorbent effect pigment as claimed in claim 1, wherein the process comprises:
   (i) optionally applying an uncalcined layer comprising or consisting of at least one of tin oxide, tin hydroxide or tin oxide hydrate to the nonmetallic substrate in platelet form,
   (ii) sequentially applying three uncalcined layers A, B and C each consisting of or comprising at least one of metal oxide, metal hydroxide or metal oxide hydrate, where the layers A, B and C are arranged directly one on top of another and where the at least one metal oxide, metal hydroxide and/or metal oxide hydrate applied in the layer B, in relation to the metal ion, is different than the metal ion(s) of the metal oxides, metal hydroxides and/or metal oxide hydrates of layer A and layer C, (iii) calcining the product obtained in step (ii) at a temperature from a range from 400° C. to 1000° C. to obtain the absorbent effect pigment comprising at least one spacer layer.

27. The process as claimed in claim 26, wherein the metal ions present in layer B diffuse at least partly into layer A and/or layer C to form the at least one spacer layer in the calcined effect pigment.

28. The process as claimed in claim 26, wherein the two or three sequentially applied metal oxides, metal hydroxides and/or metal oxide hydrates for production of the layers B and C or the layers A, B and C do not comprise any metal ion selected from the group of the metals consisting of Si, Mg and Al.

29. A process for producing the absorbent effect pigment as claimed in claim 1, wherein the process comprises:

(i) sequentially applying two uncalcined layers B and C each consisting of or comprising at least one of metal oxide, metal hydroxide or metal oxide hydrate to a calcined, singly or multiply coated nonmetallic substrate, where the layers B and C are arranged directly one on top of another and where the at least one metal oxide, metal hydroxide and/or metal oxide hydrate applied in the layer B, in relation to the metal ion, is different than the metal ion(s) of the metal oxide, metal hydroxide and/or metal oxide hydrate of layer C and of the layer which directly adjoins layer B in the substrate direction, (ii) calcining the product obtained in step (i) at a temperature from a range from 400° C. to 1000° C. to obtain the absorbent effect pigment comprising at least one spacer layer.

30. The method according to claim 29, wherein the metal ions present in layer B diffuse at least partly into layer A and/or layer C to form the at least one spacer layer in the calcined effect pigment.

31. A process for producing a pigmented cosmetic formulation, plastic, film, textile, ceramic material, glass, paint, printing ink, writing ink, varnish, powder coating or a material for a functional application comprising introducing the absorbent effect pigment of claim 1 into a cosmetic formulation, plastic, film, textile, ceramic material, glass, paint, printing ink, writing ink, varnish, powder coating or a material for a functional application.

32. The process according to claim 31, wherein the functional application is laser marking, IR reflection, or photocatalysis.

33. An article comprising at least one absorbent effect pigment as claimed in claim 1.

* * * * *

UNITED STATES PATENT AND TRADEMARK OFFICE
CERTIFICATE OF CORRECTION

PATENT NO. : 10,391,043 B2
APPLICATION NO. : 15/536220
DATED : August 27, 2019
INVENTOR(S) : Michael Grüner et al.

Page 1 of 1

It is certified that error appears in the above-identified patent and that said Letters Patent is hereby corrected as shown below:

In the Claims

Column 58, Line 6, Claim 18, delete "n>1.8" and insert -- n>1.8, --

Column 58, Line 17, Claim 18, delete "51% 99%," and insert -- 51% to 99%, --

Column 60, Line 12, Claim 30, delete "method" and insert -- process --

Signed and Sealed this
Twelfth Day of November, 2019

Andrei Iancu
*Director of the United States Patent and Trademark Office*